United States Patent
Welsh et al.

(10) Patent No.: US 10,004,212 B2
(45) Date of Patent: Jun. 26, 2018

(54) TRANSGENIC PIG MODELS OF CYSTIC FIBROSIS

(71) Applicant: University of Iowa Research Foundation, Iowa City, IA (US)

(72) Inventors: Michael J. Welsh, Riverside, IA (US); David Stoltz, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days. days.

(21) Appl. No.: 15/494,738

(22) Filed: Apr. 24, 2017

(65) Prior Publication Data
US 2017/0258058 A1    Sep. 14, 2017

Related U.S. Application Data

(62) Division of application No. 14/355,704, filed as application No. PCT/US2012/063291 on Nov. 2, 2012, now Pat. No. 9,661,831.

(60) Provisional application No. 61/555,348, filed on Nov. 3, 2011.

(51) Int. Cl.
*A01K 67/027* (2006.01)

(52) U.S. Cl.
CPC ...... *A01K 67/0278* (2013.01); *A01K 67/0276* (2013.01); *A01K 2207/15* (2013.01); *A01K 2217/056* (2013.01); *A01K 2217/072* (2013.01); *A01K 2217/206* (2013.01); *A01K 2227/108* (2013.01); *A01K 2267/0306* (2013.01)

(58) Field of Classification Search
CPC .................................................. A01K 67/0278
See application file for complete search history.

(56) References Cited

U.S. PATENT DOCUMENTS

| | | |
|---|---|---|
| 8,618,352 B2 | 12/2013 | Welsh et al. |
| 8,912,386 B2 | 12/2014 | Welsh et al. |
| 2009/0022685 A1 | 1/2009 | Lowe et al. |
| 2009/0235368 A1 | 9/2009 | Welsh et al. |
| 2009/0241203 A1 | 9/2009 | Welsh et al. |
| 2010/0041743 A1 | 2/2010 | Bosze et al. |

FOREIGN PATENT DOCUMENTS

WO   WO-2008/121199 A2   10/2008

OTHER PUBLICATIONS

Grubb et al., "Pathophysiology of gene-targeted mouse models for cystic fibrosis," Physiol Rev. 79(1 Suppl):S193-214 (1999).
Guilbault et al., "Cystic fibrosis mouse models," Am J Respir Cell Mol Biol. 36(1):1-7 (2007).
Harris, "Towards an ovine model of cystic fibrosis," Human Molecular Genetics. 6(13):2191-3 (1997).
International Preliminary Report on Patentability for PCT/US2012/063291, dated May 6, 2014 (6 pages).
International Search Report and Written Opinion for International Application No. PCT/US2012/063291, dated Jan. 8, 2013 (6 pages).
Keiser et al., "New animal models of cystic fibrosis: what are they teaching us?" available in PMC Mar. 13, 2013, published in final edited form as: Curr Opin Pulm Med. 17(6):478-83 (2011) (10 pages).
Kelly et al., "In vivo activation of the cystic fibrosis transmembrane conductance regulator mutant deltaF508 in murine nasal epithelium," Proc Natl Acad Sci U S A. 94(6):2604-8 (1997).
Meyerholz et al., "Pathology of gastrointestinal organs in a porcine model of cystic fibrosis," Am J Pathol. 176(3):1377-89 (2010).
Oppenheimer et al., "Pathology of cystic fibrosis review of the literature and comparison with 146 autopsied cases," Perspect Pediatr Pathol. 2:241-78 (1975).
Ostedgaard et al., "Cystic fibrosis transmembrane conductance regulator with a shortened R domain rescues the intestinal phenotype of CFTR-/- mice," Proc Natl Acad Sci USA. 108(7):2921-6 (2011).
Ostedgaard et al., "The (delta)F508 mutation causes CFTR misprocessing and cystic fibrosis-like disease in pigs," Sci Transl Med. 3(74):74ra24 (2011) (24 pages).
Prather et al., "Genetically engineered pig models for human diseases," available in PMC Jun. 9, 2015, published in final edited form as: Annu Rev Anim Biosci. 1:203-19 (2013) (21 pages).
Rogers et al., "Disruption of the CFTR gene produces a model of cystic fibrosis in newborn pigs," Science. 321(5897):1837-41 (2008) (10 pages).
Rogers, "The porcine lung as a potential model for cystic fibrosis," Am J Physiol Lung Cell Mol Physiol. 295(2):L240-63 (2008).
Snouwaert et al., "An animal model for cystic fibrosis made by gene targeting," Science. 257(5073):1083-8 (1992).
Stoltz et al., "Intestinal CFTR expression alleviates meconium ileus in cystic fibrosis pigs," J Clin Invest. 123(6):2685-93 (2013).
Welsh et al., Part 21: Membrane Transport Disorders, Chapter 201: Cystic Fibrosis. The Online Metabolic & Molecular Bases of Inherited Disease. The McGraw-Hill Companies, Inc., 2001 (191 pages).
Yoshida et al., "Neonatal Fc receptor for IgG regulates mucosal immune responses to luminal bacteria," J Clin Invest. 116(8):2142-2151 (2006).

(Continued)

*Primary Examiner* — Valarie E Bertoglio
(74) *Attorney, Agent, or Firm* — Clark & Elbing LLP; Susan M. Michaud

(57) ABSTRACT

This invention relates to transgenic pig models of cystic fibrosis, cells that can be used to make such animals, and methods of making and using these pigs and cells.

10 Claims, 17 Drawing Sheets

(56) References Cited

OTHER PUBLICATIONS

Zhou, "Correction of lethal intestinal defect in a mouse model of cystic fibrosis by human CFTR," Science. 266(5191):1705-8 (1994).

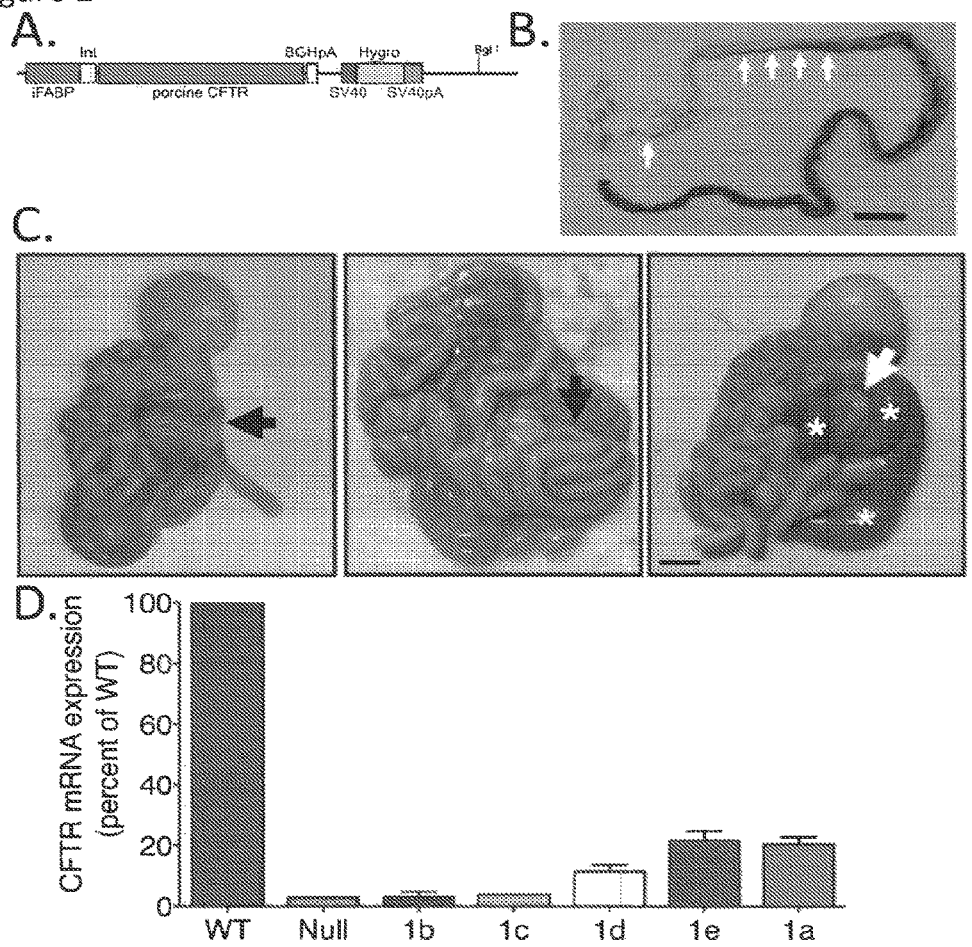

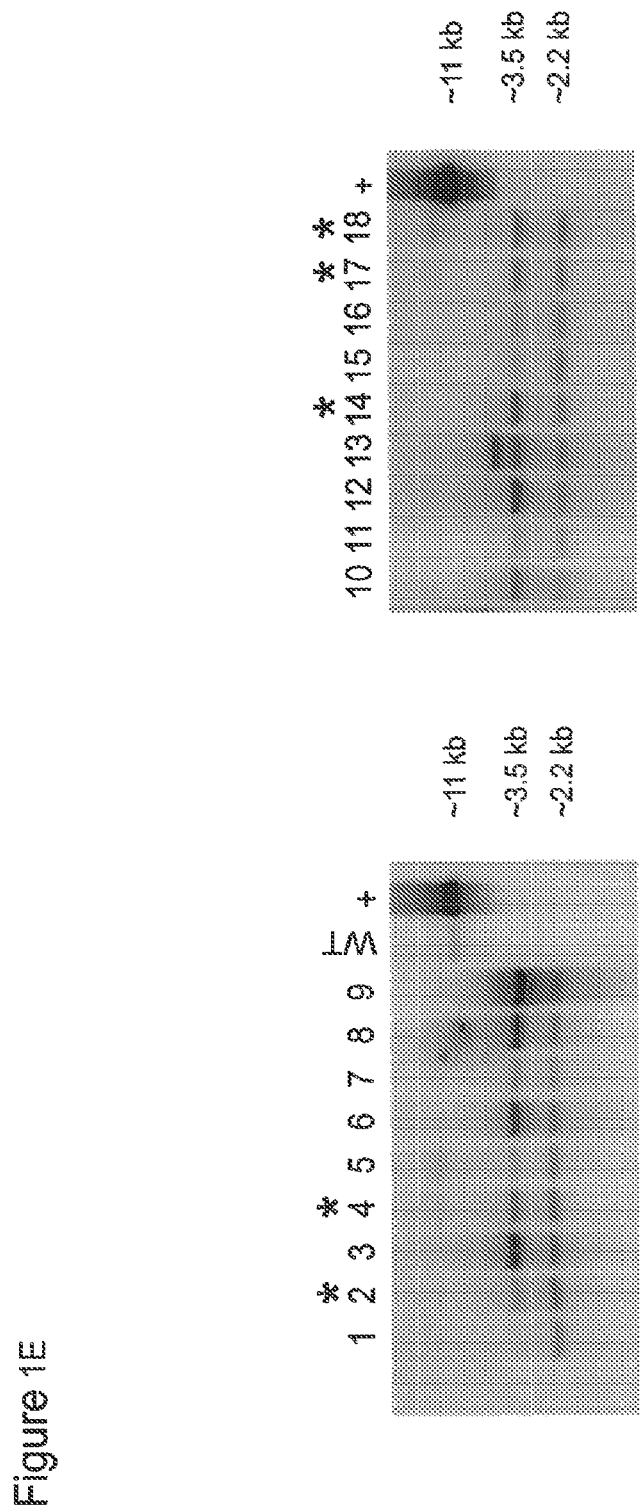

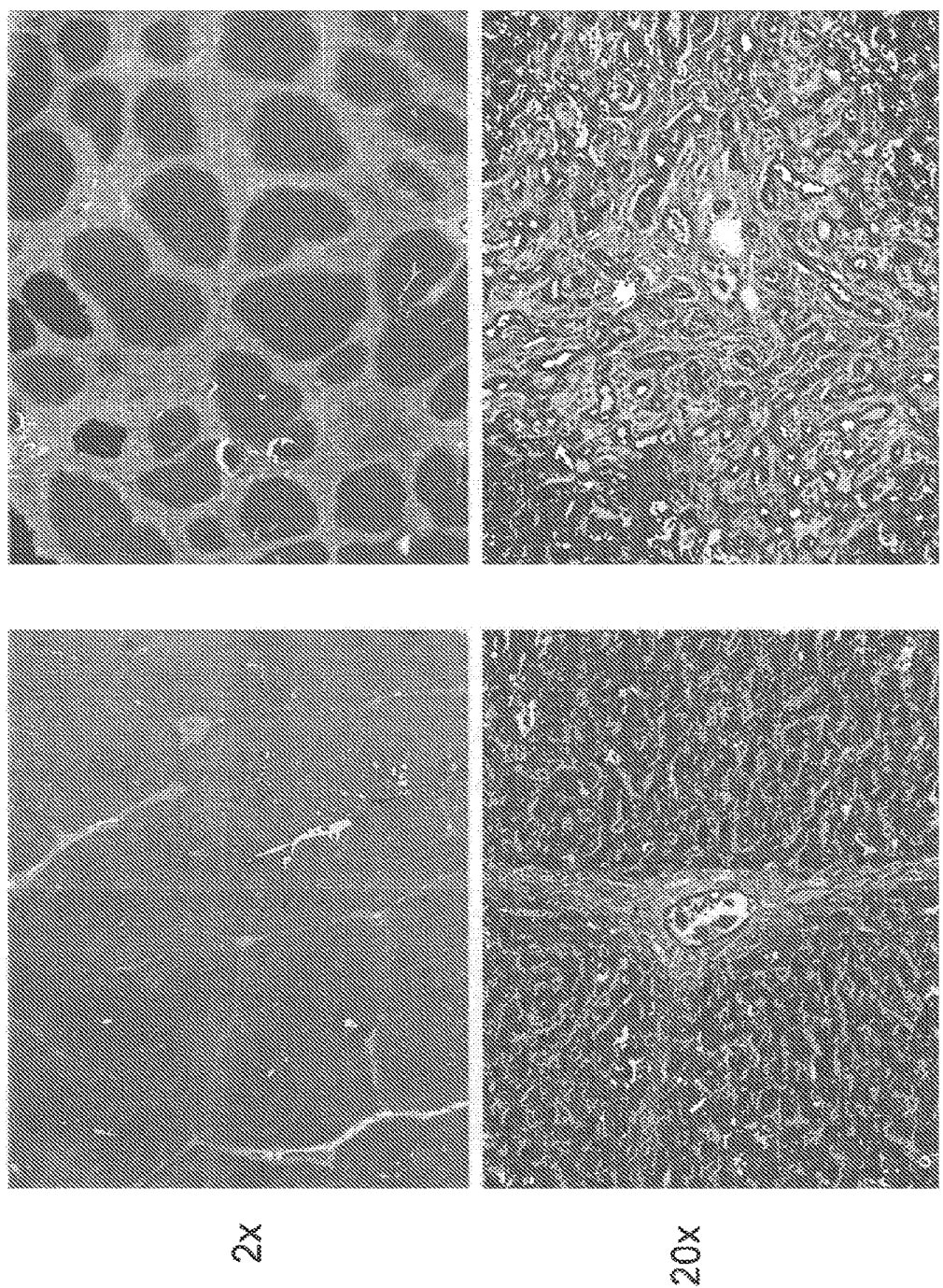

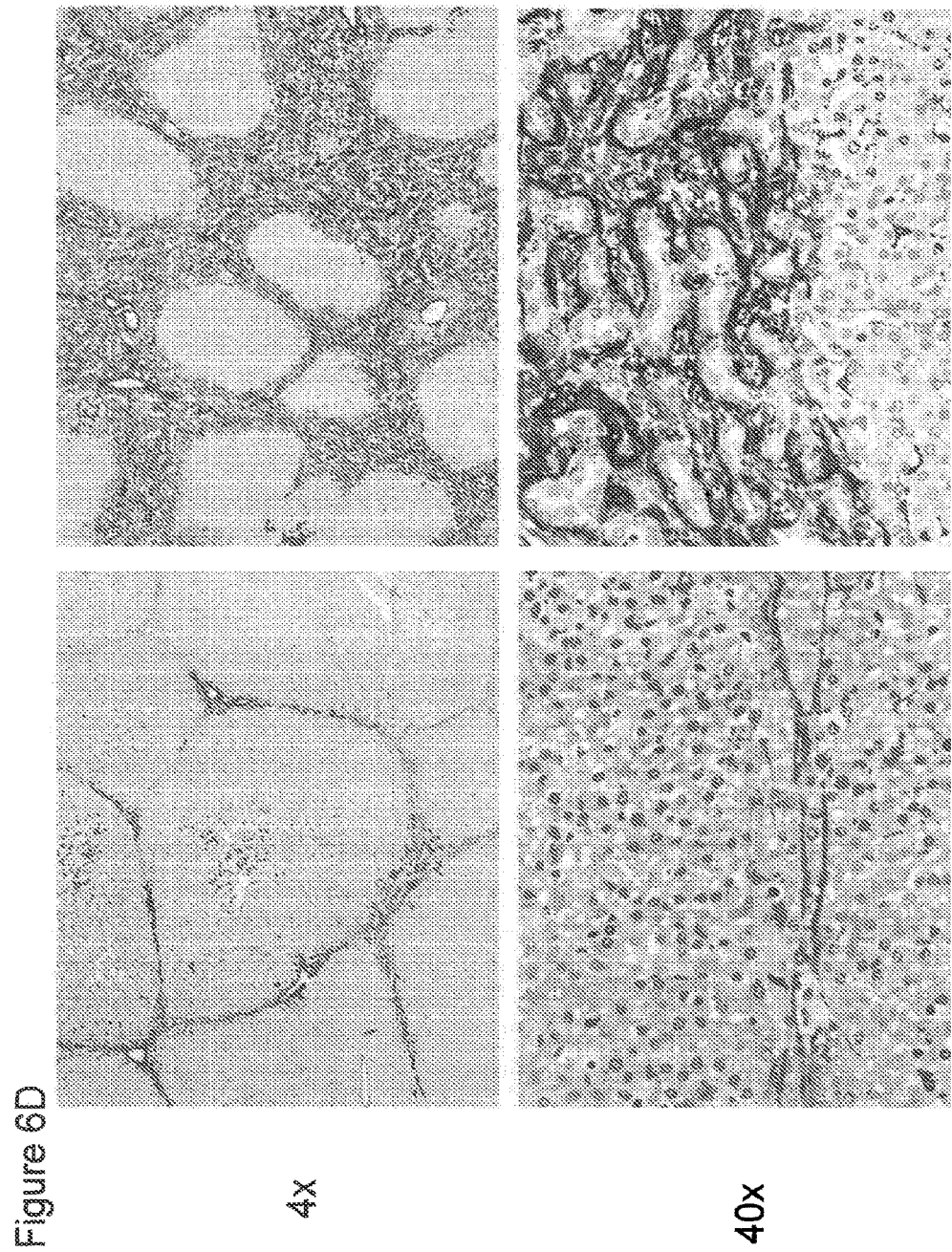

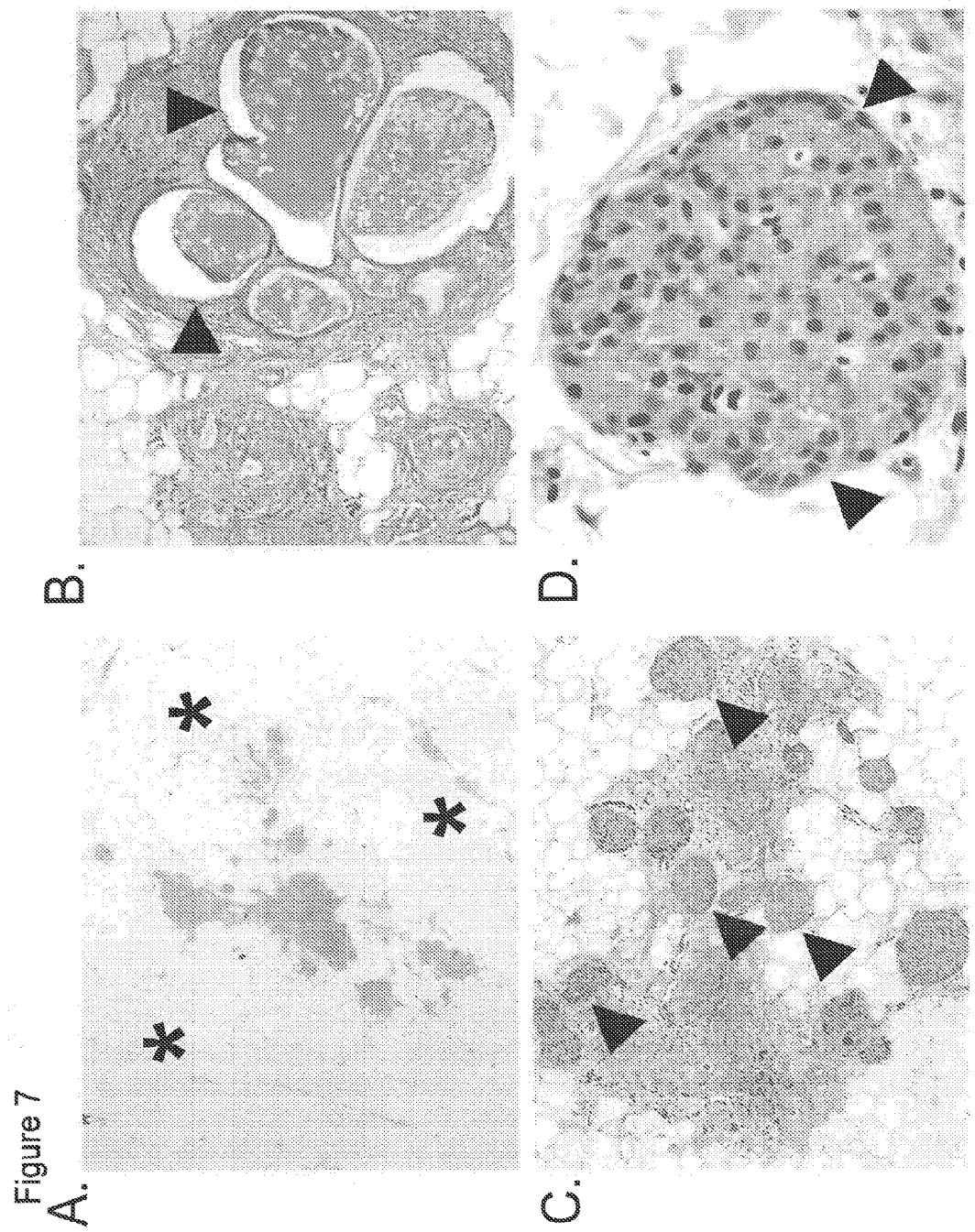

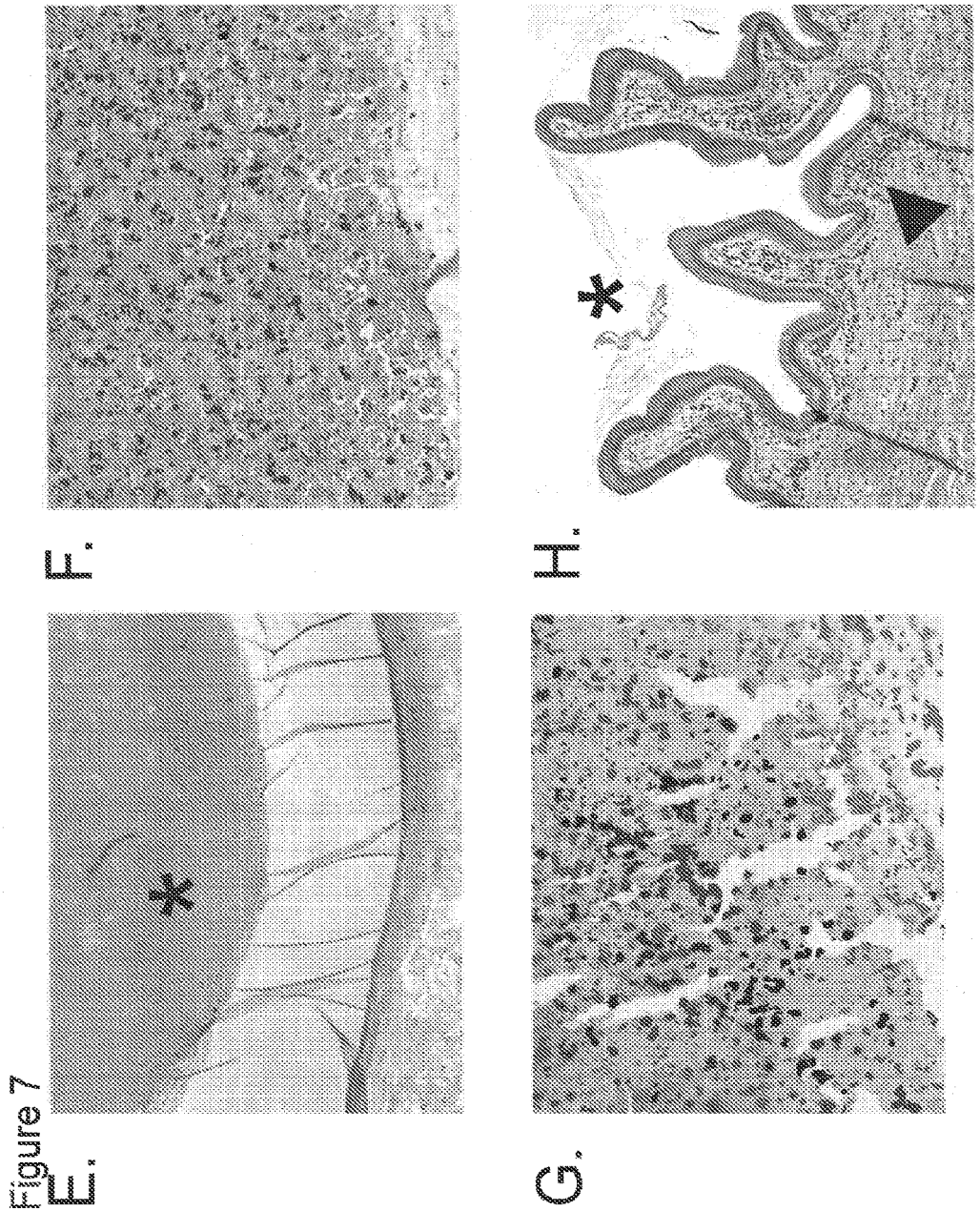

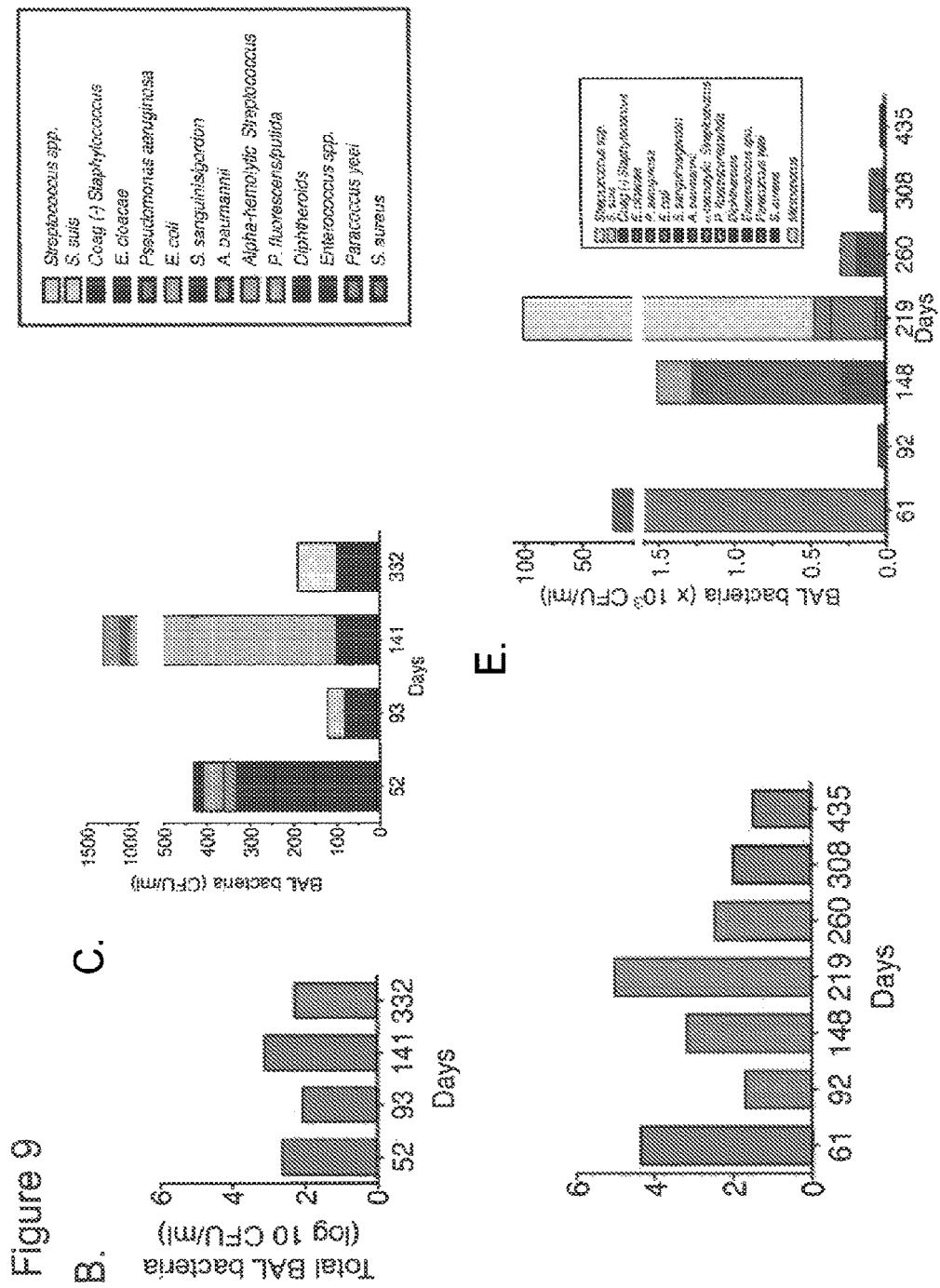

TRANSGENIC PIG MODELS OF CYSTIC FIBROSIS

CROSS-REFERENCE TO RELATED APPLICATIONS

This application is a divisional of U.S. Ser. No. 14/355,704, filed May 1, 2014 (now U.S. Pat. No. 9,661,831), which is the U.S. national stage entry under 35 U.S.C. § 371 of PCT/US2012/063291, filed Nov. 2, 2012, which claims benefit under 35 U.S.C. § 119(e) of U.S. Ser. No. 61/555,348, filed Nov. 3, 2011, the contents of which are incorporated herein by reference.

STATEMENT AS TO FEDERALLY SPONSORED RESEARCH

This invention was made with government support under grant number HL051670 awarded by the National Institutes of Health. The Government has certain rights in the invention.

FIELD OF THE INVENTION

This invention relates to transgenic pig models of cystic fibrosis, cells that can be used to make such animals, and methods of making and using these pigs and cells.

BACKGROUND OF THE INVENTION

Cystic fibrosis (CF) is caused by genetic mutations in the gene encoding the cystic fibrosis transmembrane conductance regulator (CFTR). Disrupted CFTR function leads to a number of clinical manifestations including intestinal obstruction, pancreatic insufficiency, focal biliary cirrhosis, infertility, and recurrent and chronic airway infections resulting in progressive respiratory disease (Welsh et al., Cystic Fibrosis. In *The Metabolic and Molecular Basis of Inherited Disease*, Scriver et al. (eds.), New York, McGraw-Hill, 2001; Rowe et al., N. Engl. J. Med. 352:1992-2001, 2005).

In human CF, approximately 10-20% of infants are born with an intestinal obstruction termed meconium ileus (van der Doef et al., Curr. Gastroenterol. Rep. 13:265-270, 2011). This obstruction, due to failed passage of meconium, most commonly occurs in the distal ileum and proximal colon and requires either conservative or surgical interventions to relieve the obstruction (Rescorla et al., World J. Surg. 17:318-325, 1993; Murshed et al., Eur. J. Pediatr. Surg. 7:275-277, 1997). The exact pathogenesis of meconium ileus remains to be determined, but likely results, in part, from defective CFTR-mediated Cl$^-$ and/or HCO$_3^-$ transport by the intestinal epithelium (Clarke et al., J.O.P. 2:263-267, 2001; Harmon et al., Nat. Med. 16:313-318, 2010; Garcia et al., J. Clin. Invest. 119:2613-2622, 2009).

In order to better understand the pathogenesis of CF, CF animal models have been developed including CF mice and more recently CF pigs and ferrets (Grubb et al., Physiol. Rev. 79:S193-214, 1999; Rogers et al., Science 321:1837-1841, 2008; Sun et al., J. Clin. Invest. 120:3149-3160, 2010). A clinical feature of these animal models is the presence of intestinal disease (Grubb et al, Am. J. Physiol. 273:C21-29, 1997; Sun et al., J. Clin. Invest. 120:3149-3160, 2010; Rogers et al., Science 321:1837-1841, 2008; Meyerholz et al., Am. J. Pathol. 176:1377-1389, 2010; Ostedgaard et al., Sci. Transl. Med. 3:74ra24, 2011). Most CF mice models have an intestinal phenotype. However, the clinical and histopathological features are more similar to the distal intestinal obstruction syndrome (DIOS) observed in older humans with CF as opposed to meconium ileus in infants with CF. For example, a small fraction of CF mice die from intestinal disease within days after birth, but most mortality occurs at the time of weaning. In addition, the intestinal obstruction seems to result from intestinal mucus accumulation as opposed to a failure to pass meconium at birth as observed in human CF (Oppenheimer et al., Bull. Johns Hopkins Hosp. 111:1-13, 192; Wilschanski et al., J. R. Soc. Med. 91 Suppl. 34:40-49, 1998).

We have recently developed a porcine model of CF (Rogers et al., J. Clin. Invest. 118:1571-1577, 2008; Rogers et al., Science 321:1837-1841, 2008; Ostedgaard et al., Sci. Transl. Med. 3:74ra24, 2011). CF pigs display many of the same features as humans with CF including meconium ileus, exocrine pancreatic destruction, focal biliary cirrhosis, micro-gallbladder, vas deferens abnormalities, and airway disease (Rogers et al., Science 321:1837-1841, 2008; Meyerholz et al., Am. J. Pathol. 176:1377-1389, 2010; Stoltz et al., Sci. Transl. Med. 2:29ra31, 2010; Ostedgaard et al., Sci. Transl. Med. 3:74ra24, 2011; Welsh et al., Cystic Fibrosis. In *The Metabolic and Molecular Basis of Inherited Disease*, Scriver et al. (eds.), New York, McGraw-Hill, 2001; Rowe et al., N. Engl. J. Med. 352:1992-2001, 2005). In contrast to humans, there is a 100% penetrance of meconium ileus in both CFTR−/− and CFTRΔF508/ΔF508 newborn piglets. Features of the CF pig meconium ileus very closely replicate that observed in humans with CF including obstruction by meconium in the distal bowel, atretic intestinal segments, and microcolon (Meyerholz et al., Am. J. Pathol. 176:1377-1389, 2010; Rogers et al., Science 321:1837-1841, 2008; Ostedgaard et al., Sci. Transl. Med. 3:74ra24, 2011). The meconium ileus in CF pigs is lethal if not corrected within 24-36 hours after birth. Limited attempts at non-surgical correction (gastrograffin enemas) of the intestinal obstruction in CF pigs have been unsuccessful, in part, due to the atretic intestinal segments. Yet, we have been able to surgically correct the meconium ileus in both CFTR−/− and CFTRΔF508/ΔF508 pigs (Rogers et al., Science 321:1837-1841, 2008; Stoltz et al., Sci. Transl. Med. 2:29ra31, 2010; Ostedgaard et al., Sci. Transl. Med. 3:74ra24, 2011). Despite the success of surgical correction of the meconium ileus in CF pigs, the surgical procedure can be associated with morbidity and mortality and is still not feasible in most CF pigs due complications associated with meconium ileus including intestinal atresia and in utero intestinal perforation.

SUMMARY OF THE INVENTION

The invention provides transgenic pigs including a genome that has (i) one or more mutations in both alleles of the pig cystic fibrosis transmembrane regulator (CFTR) gene resulting in altered pig CFTR expression and one or more symptoms of cystic fibrosis (CF) in the pigs; and (ii) a CFTR transgene (e.g., a wild-type or other functional CFTR transgene; e.g., a human or porcine gene) under the control of promoter resulting in CFTR expression in intestinal cells of the pigs (e.g., an intestinal cell-specific promoter (e.g., an intestinal fatty acid binding protein (iFABP) promoter, such as that of a rat)). The pigs of the invention exhibit reduced meconium ileus relative to pigs lacking expression of a CFTR transgene in intestinal cells. As described further herein, the pigs of the invention can have one or more phenotypes selected from the group consisting of (a) an electrophysiological phenotype similar to that of human cystic fibrosis, (b) pancreatic insufficiency or abnormalities, (c) hepatic abnormalities, (d) gall bladder and/or bile duct abnormalities, (e) tracheal abnormalities, (f) cystic fibrosis lung disease, (g) sweat gland abnormalities, and (h) kidney abnormalities. In certain examples, the CFTR alleles of the genomes of pigs have been knocked out and/or replaced with mutant CFTR genes (e.g., human or porcine genes), the expression of which results in a CF phenotype. In one example, the mutant CFTR gene (e.g., human or porcine gene) includes a deletion of F508.

The invention also provides methods of determining whether a candidate therapeutic approach can be used in the treatment of cystic fibrosis. These methods involve carrying out a therapeutic approach (e.g., administering a candidate therapeutic agent) to a transgenic pig as described herein, and monitoring the pig for a symptom of cystic fibrosis. Detection of improvement in a symptom of cystic fibrosis indicates the identification of a therapeutic approach (e.g., a candidate therapeutic agent, such as a candidate compound) that can be used in the treatment of cystic fibrosis. In certain examples, the symptom of cystic fibrosis is monitored in the lung, pancreas, liver, or kidney of the pig.

Also included in the invention are isolated cells or tissues of the pigs of the invention, homozygous and heterozygous forms of the pigs of the invention, and isolated cells and tissues thereof. Further, cells used to make the animals of the invention are included in the invention.

Other features and advantages of the invention will be apparent from the drawings, the detailed description, the experimental examples, and the claims.

BRIEF DESCRIPTION OF THE DRAWINGS

FIG. 1. (A) Schematic of the transgene vector (10871 bp) with porcine CFTR cDNA (1790-6238) driven by the rat intestinal fatty acid binding protein (iFABP) promoter (209-1419), flanked by the intervening sequence and the bovine growth hormone poly-A (BGHpA) (6295-6508), and followed by a hygromycin cDNA sequence (7392-8415) flanked by SV40 (7049-7373) and SV40 poly-A (8428-8800) signal sequences. Bgl I restriction site is denoted. (B) Gross image of a meconium plug (green-black colored portion of stool) that was passed by a CFTR−/−; Tg-FABP-pCFTR pig (line 1e) following an enema at approximately 18 h after birth. After the meconium plug was passed, a transition to normal-appearing stool was observed (yellow-green stool denoted by white arrows) bar=2 cm. (C) Gross images from the gastrointestinal tract of CFTR−/−; Tg-FABP-pCFTR piglets. At birth, in 2 of the 5 lines meconium ileus was alleviated in CFTR−/−; Tg-FABP-pCFTR pigs. Meconium ileus lesions ranged from absent (left panel, line 1a) with normal sized intestine and colon (black arrow) to severe meconium obstruction (right panel, line 1c, white asterisks) often located in the spiral colon with distal microcolon (white arrow). Middle panel—Gross image from the intestinal tract of a CFTR−/−; Tg-FABP-pCFTR pig (line 1a) at 6 d of age. The intestine and spiral colon (arrow) is of normal size and coloration. bar=1.3 cm. (D) CFTR mRNA expression in ileal segments from CFTR+/+, CFTR−/−, and CFTR−/−; TgFABP-pCFTR newborn piglets. CFTR mRNA levels were determined with quantitative RT-PCR (relative to beta-actin) and values are expressed as a percentage of CFTR mRNA levels relative to CFTR+/+ levels. n=2-4 per genotype. Bars represent mean±SEM. (E) Southern blot of amplified genomic DNA from rat iFABP-pCFTR transgenic pig fetal CFTR−/− fibroblasts. Ban11-digested amplified genomic DNA was hybridized with a probe that detected exon 13 of porcine CFTR. Endogenous CFTR yields a ~2.2 kb band and iFABP-pCFTR ~3.5 kb. Lanes 1-18 contain DNA from individual fibroblast clones. WT well contains DNA from a wild-type control pig. Positive control (+) well contains the linearized iFABP-pCFTR plasmid construct. Clones 1E (lane 2), 1A (lane 4), 1D (lane 14), 1C (lane 17), and 1B (lane 18) were selected for somatic cell nuclear transfer into enucleated oocytes.

FIG. 7. Microscopic images of the pancreas from cases #4 (332 d) and #5 (435 d). (A) Remnant exocrine pancreas was composed mostly of adipose tissue (asterisks) with sparse remnant pancreas. (B) Dilated cystic ducts (arrows). (C) and (D) show remnant pancreas composed of scant exocrine tissue and intact islets (arrows). HE stain. (E-H) Microscopic images of the gallbladder from cases #4 and #5. (E) There is mucopurulent and necrotic debris in the gallbladder lumen (asterisk). In the necrotic areas, there were many (F) cellular foci (G) dense calcifications (black staining) and (H) inflammatory cells (arrow) and luminal mucus (asterisk).

DETAILED DESCRIPTION OF THE INVENTION

Figure 2:
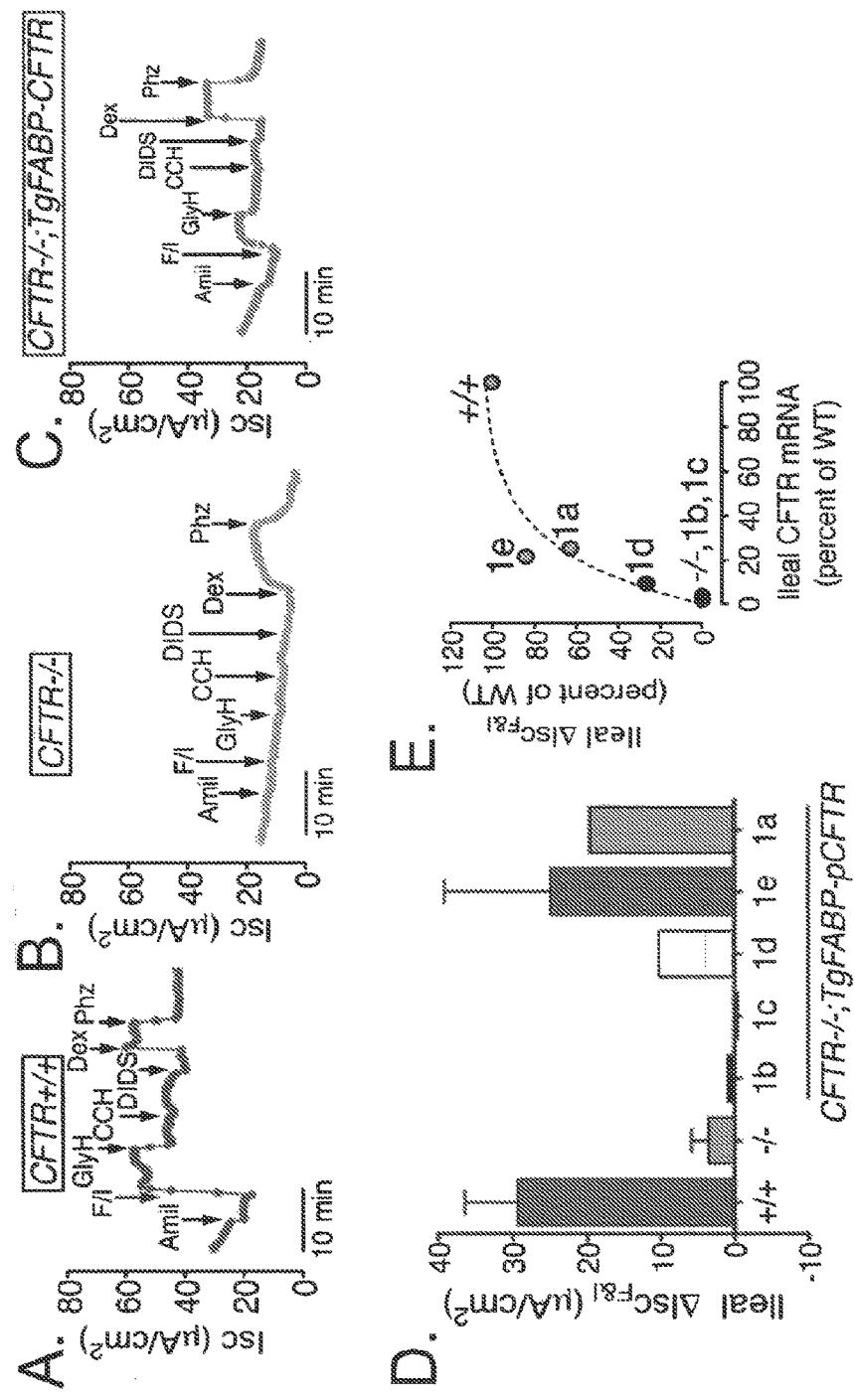
FIG. 2. (A-E) Representative Isc tracings from excised ileal segments mounted in Ussing chambers for electrophysiological studies. (A) CFTR+/+, (B) CFTR−/−, (C) CFTR−/−; Tg-iFABP-pCFTR. Tissue samples were obtained from newborn piglets. The following agents were added sequentially: apical 100 µm amiloride (amil), apical 10 forskolin (F)/100 µm IBMX (I), apical 100 µm GlyH, basolateral 100 µm carbachol (CCH), apical 100 µm DIDS, apical 5 mM dextrose (Dex), and apical 200 µm phlorizin (Phz). (D) Changes in Isc following addition of forskolin/IBMX to freshly excised ileal segments from newborn CFTR+/+ (n=8), CFTR−/− (n=7), and CFTR−/−; TgFABP-pCFTR (n=1 for 1b, 3 for 1c, 3 for 1d, 4 for 1e, and 2 for 1a) piglets. Prior to forskolin/IBMX treatment, tissues were exposed to amiloride. Bars represent mean±SEM. (E) Ileal short-circuit current following forskolin and IBMX treatment versus ileal CFTR mRNA. All data are shown as a percentage of wild-type levels. Red circles denote cell lines (litters) that had a severe meconium ileus phenotype and green circles denote cell lines (litters) that had a reduction in the severity of meconium ileus.

The invention provides transgenic pig models of cystic fibrosis (CF) in which the meconium ileus phenotype of the pigs is reduced or alleviated by intestinal expression of the cystic fibrosis transmembrane regulator (CFTR). As discussed in detail above, meconium ileus is a condition characterized by intestinal obstruction, which is caused by failed passage of meconium, the material present in the bowel prior to birth. We have found that meconium ileus has 100% penetrance and is lethal in our transgenic pig CF models if not corrected within 24-36 hours after birth. Prior to the present invention, correction has involved surgery, which can be associated with morbidity and mortality, and is quite difficult in most CF pigs due to complications associated with their condition. The present invention eliminates the need for surgery, and thus provides pig models of CF in which post-natal care can be simplified. This provides the opportunity for use and study of the models, without complications associated with surgery.

The pigs of the invention are CF models due to mutation and/or inactivation of both alleles of their endogenous CFTR gene. This is achieved by, for example, knock out of CFTR alleles and/or replacement of CFTR alleles with mutant CFTR sequences (e.g., porcine or human CFTR sequences having, for example, the ΔF508 mutation). The pigs can be produced using homologous recombination and somatic cell nuclear transfer methods, such as those described in U.S. Pat. No. 7,989,675; US-2009-0241203-A1; Rogers et al., Science 321:1837-1841, 2008; Rogers et al., J. Clin. Invest. 118(4):1571-1577, 2008; Ostedgaard et al., Sci. Transl. Med. 3(74):74ra24, 2011, the teachings of which are incorporated herein by reference.

According to the invention, the meconium ileus phenotype is corrected or alleviated in CF pig models, such as those described above, by expression of CFTR (e.g., wild-type CFTR) in intestinal cells of the pig. This can be achieved by use of an intestinal cell-specific promoter. A construct expressing CFTR can be, for example, introduced into the genome of a CF model pig by somatic cell nuclear transfer. Preferably, the promoter is specific for intestinal cells so that the correction is limited to the intestinal phenotype, including meconium ileus. This was achieved using the iFABP promoter, as described in the experimental examples set forth below. In addition to this promoter, other promoters can be used including, e.g., the liver FABP promoter and the villin promoter. Further, in addition to intestinal cell-specific promoters, those having somewhat broader expression, but still resulting in the maintenance of some CF phenotypes, can be used. The CFTR gene expressed under the control of such a promoter can be, for example, porcine or human CFTR (e.g., wild-type porcine or human CFTR).

The levels of expression of CFTR in intestinal cells, as well as the specific cell types in which expression is achieved, can vary, as determined to be appropriate by those of skill in the art. Appropriate levels can be determined by assessment of animals for a desired phenotype, such as correction or alleviation of meconium ileus. As general guidance, and based on the experiments described herein, appropriate levels include CFTR expressed at a level greater than 10% of that of a comparable sample from a CFTR+/CFTR+ pig, preferably at least 20%, 30%, 40%, 50%, 75%, 100%, or more, as determined by analysis of mRNA expression levels in samples prepared from excised ileal segments, as described below. As additional guidance, appropriate levels include CFTR expression that leads to more than 27%, preferably 60% or more, of that of a comparable sample from a CFTR+/CFTR+ pig, CFTR activity, as determined by analysis of forskolin and IBMX-stimulated increased short-circuit current in ileal segments, as described below. Also, as explained further below, the level of intestinal expression of CFTR correlates with the intestinal phenotype.

The levels of meconium ileus in pigs of the invention can vary between only a small improvement up to 100% improvement (e.g., 10%, 25%, 50%, 75%, 90%, 95% and 99%), as compared with CFTR−/CFTR− and wild-type, CFTR+/CFTR+ animals. The meconium ileus can be assessed by methods known in the art, such as those described herein, including assessment of intestinal blockage by direct analysis of tissue or attempted evacuation of any meconium present, or by electrophysiological analysis of affected tissues, as described herein.

Although the meconium ileus phenotype of the pigs of the invention is corrected or alleviated, the pigs maintain other phenotypes of cystic fibrosis. Thus, the pigs of the invention can be characterized by one or more phenotypes including abnormalities in the lungs, other parts of the respiratory tract, pancreas, liver, gall bladder, and vas deferens. Such abnormalities may include infection and inflammation of any or all of the organs noted above, irregularities in tracheal shape and defects in tracheal cartilage rings, focal biliary cirrhosis, progressive loss of exocrine pancreatic tissue and replacement by adipose tissue, gallbladder of small size and including mucus and cellular debris, collapse or absence of the lumen of the vas deferens, and electrophysiological abnormalities. In more detail, such abnormalities may include one or more of the following:

(i) electrophysiological features similar to CF humans including, e.g., any one or more of (a) hyperpolarized baseline Vt, (b) reduction of Vt by amiloride, and (c) no CFTR or other Cl⁻ channel activity (as measured by, e.g., perfusion of apical surface with Cl⁻-free solution and addition of isoproterenol; perfusion with ATP to activate P2Y2 receptors and $Ca^{2+}$-activated Cl⁻ channels; and perfusion with the CFTR inhibitor GlyH-101);

(ii) exocrine pancreatic insufficiency or abnormalities, as characterized by, e.g., one or more of (a) decreased size, (b) degenerative lobules with, e.g., increased loose adipose and myxomatous tissue, and scattered to moderate cellular inflammation, (c) diminished eosinophilic zymogen granules in residual acini, (d) variable dilation and obstruction of centroacinar spaces, ductules, and ducts with eosinophilic material plus infrequent neutrophils and macrophages mixed with cellular debris, (e) foci of mucinous metaplasia in ducts and ductules, and (f) increased redness;

(iii) hepatic abnormalities consistent with focal biliary cirrhosis, as characterized by, e.g., any one or more of (a) mild to moderate hepatic lesions, (b) chronic cellular inflammation, (c) ductular hyperplasia, and (d) mild fibrosis;

(iv) gall bladder and/or bile duct abnormalities, as characterized by, e.g., any one or more of (a) gallstones, (b) reduced size, (c) congealed bile and mucus, and (d) epithelia with diffuse mucinous changes with folds extending into the lumen;

(v) tracheal abnormalities characterized by, for example, altered lumen area, circumference, submucosal gland area, and smooth muscle area;

(vi) characteristics of CF lung disease, for example, any one or more of obstruction of some airways with mucopurulent material, scattered mucopurulent debris in airway lumens with chronic purulent to lymphoid airway wall inflammation, surface epithelium with areas of goblet cell hyperplasia, mucocellular material in submucosal glands, lobular atelectasis, host defense defect as shown by detection of a variety of bacterial species in lung samples; and (vii) lack of abnormalities in vas deferens and lungs at birth.
Additional information concerning the phenotypes of pigs of the invention is provided below.

The pigs of the invention can be used in screening methods including those carried out in the identification and characterization of approaches for treating CF. Candidate drugs and other approaches to treatment can therefore be evaluated for effects on CF symptoms in the pigs of the invention. Thus, in addition to the pig models themselves, the invention also provides methods of using the animals for identifying and characterizing treatments. Further, the invention includes methods of making the pigs of the invention, as well as cells that can be used in these methods. Additional details concerning the pig models systems, methods, and cells of the invention are provided as follows.

The animals of the invention can be made using the following general strategy. Briefly, the genome of a cell (e.g., a fetal fibroblast or another cell) from a pig of interest, such as a CFTR−/− pig or a CFTR ΔF508/ΔF508 pig (wherein the mutant CFTR gene is, e.g., porcine or human), is genetically modified by introduction of one or more CFTR genes under the control of an intestinal cell-specific promoter, preferably by transfection (e.g., using electroporation) or by gene targeting by homologous recombination to create a "donor cell." The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. Typically, the donor cell, oocyte, and surrogate female are of the same species, but the sources can be different species, as is known in the art. The invention includes cells of the pigs of the invention, as well as cells used in making the pigs of the invention (e.g., a CFTR−/− or a CFTR ΔF508/ΔF508 cell comprising an integrated CFTR transgene under the control of an intestinal cell-specific promoter, as described herein).

Details of methods for making large genetically modified animals, such as pigs, used in the invention, are provided, for example, in U.S. Pat. No. 7,989,675; US-2009-0241203-A1; Rogers et al., Science 321:1837-1841, 2008; Rogers et al., J. Clin. Invest. 118(4):1571-1577, 2008; Ostedgaard et al., Sci. Transl. Med. 3(74):74ra24, 2011. Additional information concerning certain aspects of such methods is known in the art and can also be adapted for use in the present invention (see, e.g., US 2005/0120400 A1; U.S. Pat. No. 5,995,577; WO 95/16670; WO 96/07732; WO 97/00669; WO 97 00668; WO 2005/104835; Lai et al., Reproductive Biology and Endocrinology 1:82, 2003; Hao et al., Transgenic Res. 15:739-750, 2006; Li et al., Biology of Reproduction 75:226-230, 2006; Lai et al., Nature Biotechnology 24(4): 435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001; the contents of each of which are incorporated herein by reference).

The transgenic pigs of the invention can be any members of the family Suidae, and in particular any member of the genus *Sus*, such as *Sus scrofa*, which is also known as the domestic pig or a subspecies thereof (*Sus scrofa domestica*). In one specific example, the animal is a miniature swine that is a descendent from the miniature swine described by Sachs et al., Transplantation 22:559, 1976. The pigs of the invention can be of any age, including piglets, juvenile pigs, and adult pigs, both female and male.

The transgenic animals of the invention can be used in the identification and characterization of drug and other treatment methods for CF. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in the case of CF animal models having impaired respiratory function, the effect of the drug on such function can be assessed by measurement of standard respiratory parameters. In another example, in the case of animals exhibiting impaired digestion, due to blockage of pancreatic and/or liver ducts, the effect of a treatment on digestion can be determined.

With the models of the invention, it is possible to test hypotheses that lead to new treatments and to evaluate potential therapies for CF lung disease. The models also make it possible to assess electrolyte transport by porcine airway epithelia in vitro and in vivo, the volume of airway surface liquid in vitro and in vivo, the ion composition of airway surface liquid in vitro and in vivo, the airway surface liquid pH in the airway, and electrolyte transport in the small airways. It is also possible to measure respiratory mucociliary transport in vitro and in vivo. For assessing inflammation, several tests and assays can be carried out, including (but not limited to) assays of key markers of inflammation in amniotic fluid, fetal lung liquid, and bronchoalveolar lavage by using lung tissue histochemistry, large-scale gene expression profiling of pulmonary tissues, cytokine and cell assays, and proteomics. It is also possible to raise CF and non-CF piglets in isolators under completely germ free conditions and to test for the development of pulmonary inflammation, and then selectively expose the piglets to inflammatory stimuli including bacteria and viruses. In addition, investigators can test how loss of CFTR function in airway epithelia results in altered NFKB signaling, the function of secreted epithelial antimicrobials/host defense proteins, and the consequences of loss of CFTR function in macrophages or neutrophils. The availability of the porcine CF model allows tests of the early manifestations of the CF. The natural history of pulmonary infections in CF pigs can also be monitored, leading to a determination of whether the airway epithelia of CF pigs can be colonized by CF or porcine pathogens and/or non-pathogenic opportunistic organisms.

Although lung disease is the current main cause of mortality, patients suffer from CF disease in many other organs. Availability of a CF model allows new investigations and tests of therapeutics in the pancreas, intestine, sweat gland, liver, vas deferens, kidney, and other organs affected primarily or secondarily by CF. The screening methods of the invention can be carried out to test the efficacy of new compounds, combinations of new and old compounds, non-pharmaceutical treatments, gene therapy, and combinations of pharmaceutical and non-pharmaceutical treatments.

The following Examples are meant to illustrate the invention and are not meant to limit the scope of the invention in any way.

EXPERIMENTAL EXAMPLES

Results
Generation of CFTR−/−; TgFABP-pCFTR Pigs

We hypothesized that intestinal expression of CFTR in CFTR−/− pigs would result in a milder form of meconium ileus, amenable to correction with conservative techniques or complete correction of the meconium ileus phenotype. We expressed CFTR in the intestinal tract under control of the rat iFABP gene promoter (Zhou et al., Science 266:1705-1708, 1994). To produce CFTR−/− gut-corrected pigs (hereafter called CFTR−/−; TgFABP-pCFTR), CFTR−/− fetal fibroblasts (male) were first transfected with a rat iFABP-pCFTR construct (FIG. 1A). Antibiotic selection was performed followed by confirmation of positive clones with Southern blotting (FIG. 1E). Positive clones were expanded and used as nuclear donors for transfer to enucleated oocytes. Somatic cell nuclear transfer (SCNT) embryos were transferred to surrogate females and piglets were delivered by cesarean section at term. Five different clones or cell lines (1a, 1b, 1c, 1d, and 1e) were transferred individually to a total of 15 surrogate females (line 1e was transferred to 8 different surrogate females). Seven surrogates produced a total of 25 male piglets. Eight surrogates did not produce offspring.

Transgenic Expression of iFABP-pCFTR Corrects the Meconium Ileus Phenotype in CFTR−/− Pigs One of the goals of this study was to determine if transgenic expression of CFTR in the intestinal tract, under the control of the iFABP promoter, would alleviate the meconium ileus in CF pigs. Not knowing if this approach would work, we decided to enhance the likelihood of meconium ileus correction by treating the majority of animals with enemas after birth. Newborn pigs (21 of the 25 piglets born) received a gastrograffin enema shortly after birth and attempts were made to keep them alive. The other 4 piglets were euthanized shortly after birth for various reasons (1 for elective necropsy, 2 for anal malformations, 1 for limb malformations).

Within 1 hour of birth, piglets underwent a gastrograffin enema and were hand-fed colostrum containing polyethylene glycol and transitioned to piglet milk replacer. The response to the enema was variable between litters. Following the initial enema, we recovered from the rectum either nothing, segments of meconium, or small white mucus plugs (~2 mm in diameter). To enhance removal of meconium from the intestinal tract, repeat gastrograffin enemas were performed at 8-12 h intervals until either all of the meconium was evacuated (FIG. 1B) or the animals failed to pass meconium despite repeal enemas. The decision to euthanize was based upon the lack of a response to enemas (no or minimal meconium output) despite good oral intake.

Of the 5 transgenic lines studied, piglets from 2 lines (1a and 1e) had a favorable intestinal phenotype. FIG. 1C shows images of the intestinal tract from a CFTR−/−; TgFABP-pCFTR newborn piglet (left panel, line 1a) and from a 6 day old CFTR−/−; TgFABP-pCFTR pig (middle panel, line 1a). There was a relatively normal-appearing small intestine, no evidence of atretic intestinal segments, and a normal-sized spiral colon. In contrast, piglets from lines 1b, 1c, and 1d had evidence of severe meconium ileus at birth (FIG. 1C, right panel), similar to CFTR−/− newborn piglets in the absence of the transgene. These findings show that expression of CFTR under the control of the rat iFABP promoter can alleviate/correct the meconium ileus phenotype in CF piglets.

CFTR mRNA Expression Levels Correlate with Intestinal Phenotype

Finding variable levels of meconium ileus correction between the individual lines suggested that CFTR mRNA expression levels differed between CFTR−/−; TgFABP-pCFTR animals from individual clones or cell lines. We first performed quantitative RT-PCR for CFTR mRNA on ileal tissue segments from CFTR+/+, CFTR−/−, and CFTR−/−; TgFABP-pCFTR newborn piglets. Compared to CFTR+/+ ileal samples, CFTR mRNA was essentially undetectable in intestinal tissues from CFTR−/− animals (FIG. 1D. In the CFTR−/−; TgFABP-pCFTR animals, we found varying levels of ileal CFTR mRNA expression between the different cell lines used for SCNT (FIG. 1D). For example, some lines (1e and 1a) showed high ileal CFTR mRNA levels, others (1b and 1c) had very low levels of CFTR mRNA in the range of those observed in CFTR−/− ileum, and one line had intermediate levels (1d). This variability was not unexpected and is consistent with differing transgene insertion sites and/or transgene copy number between the different cell lines used for SCNT.

We next asked if CFTR mRNA levels correlated with intestinal disease phenotype. CFTR−/−; TgFABP-pCFTR piglets with the highest CFTR mRNA levels had the least severe meconium ileus and were more likely to survive (Table 1). Lines in which the meconium ileus phenotype was not corrected showed ileal CFTR mRNA levels less than 10% of values from CFTR+/+ ileum (line 1b=1.9%, line 1c=3.7%, and line 1d 9.4%). Much higher levels were observed in the two lines that had a favorable intestinal phenotype. Lines 1e and 1a had ileal CFTR mRNA levels at 21.7 and 25.5%, respectively, of levels in CFTR+/+ pigs. These data suggest that severe meconium ileus occurs with ileal CFTR mRNA levels less than approximately 10% of wild-type levels, but that approximately 22% of wild-type CFTR mRNA expression is sufficient to prevent meconium ileus in CFTR−/− pigs.

TABLE 1

| Litter | Meconium ileus Phenotype | % wild-type CFTR-mRNA | % wild-type $ISC_{cAMP}$ |
|---|---|---|---|
| CFTR−/− | 3+ | 3.5 | 0 |
| Tg-FABP-pCFTR 1b | 3+ | 1.9 | 0 |
| Tg-FABP-pCFTR 1c | 3+ | 3.7 | 0 |
| Tg-FABP-pCFTR 1d | 2+ | 9.4 | 27 |
| Tg-FABP-pCFTR 1e | 1+ | 21.7 | 84 |
| Tg-FABP-pCFTR 1a | 1+ | 25.5 | 63 |
| CFTR+/+ | 0 | 100 | 100 |

Transgenic Expression of iFABP-pCFTR in CFTR−/− Pigs Increases CFTR Expression in Intestinal Crypts To test for the presence of CFTR protein in intestinal epithelia, immunohistochemistry was performed on ileal samples from CFTR+/+, CFTR−/−, and CFTR−/−; TgFABP-pCFTR newborn piglets. CFTR localized to the apical membrane component of crypt, but not villous cells in CFTR+/+ tissues. No CFTR was detected in CFTR−/− tissues (FIG. 1E). CFTR was variably present in ileum from the different CFTR−/−; TgFABP-pCFTR lines and was most consistently detected in the lines with the favorable intestinal phenotype (FIG. 1E). In contrast to the villous cell localization of human CFTR expressed under control of the rat iFABP promoter (Zhou et al., Science 266:1705-1708, 1994) or villin promoter (Lu et al., Pediatr. Pulmonol. Suppl. 12:213, 1995) in mice, porcine CFTR localized to crypt cells in the CFTR−/−; TgFABP-pCFTR intestines (FIG. 1E). This finding is in agreement with other reports of endogenous CFTR localization in the intestinal crypt cells (Rogers et al., Science 321:1837-1841, 2008; Odes et al., Acta Physiol. Scand. 178:231-240, 2003; Trezise et al., Nature 353:434-437, 1991; Strong et al., J. Clin. Invest. 93:347-354, 1994).

Transgenic Expression of iFABP-pCFTR in CFTR−/− Pigs Increases Intestinal CFTR-Mediated Cl⁻ Transport We next asked if iFABP promoter driven expression of CFTR led to functional CFTR activity in the intestine. Excised ileal segments were mounted in Ussing chambers and transepithelial currents were assayed. Addition of forskolin and 3-isobutyl-2-methylxanthine (IBMX), to increase cellular concentrations of cAMP and phosphorylate and activate CFTR, increased short-circuit current (Isc) in ileal segments of CFTR+/+ intestine, but failed to induce a significant response in CFTR−/− intestine (FIGS. 2A and 2B).

Similar to the variable CFTR mRNA levels observed across the different CFTR−/−; TgFABP-pCFTR cell lines, we also observed a range of forskolin and IBMX-stimulated Isc in ileum from transgenic animals. Lines 1a and 1e had forskolin and IBMX responses in the range of wild-type tissue, while ileum from 1b and 1c failed to respond to forskolin and IBMX (similar to CFTR−/− tissue), and line 1d had an intermediate phenotype (FIGS. 2A-2D). Compared to the forskolin and IBMX response observed from CFTR+/+ ileal tissues, the average ileal response in samples from lines 1a and 1e were 63 and 84% of control tissue values, respectively. The forskolin and IBMX Isc values in lines 1b and 1c were similar to CFTR−/− and line 1d was 27% of CFTR+/+ (FIG. 2D and Table 1).

The forskolin and IBMX response in ileal segments correlated very well with the intestinal phenotype observed between the different CFTR−/−; TgFABP-pCFTR lines. For example, lines 1a and 1e had the greatest forskolin and IBMX Isc responses and the least severe intestinal phenotype. Furthermore, 27% of wild-type CFTR-mediated Cl⁻ transport in the ileum is not sufficient to prevent meconium ileus, but 63% of wild-type function does correct and/or alleviate the meconium ileus phenotype in CFTR−/− pigs (FIG. 2E).

Figure 3:
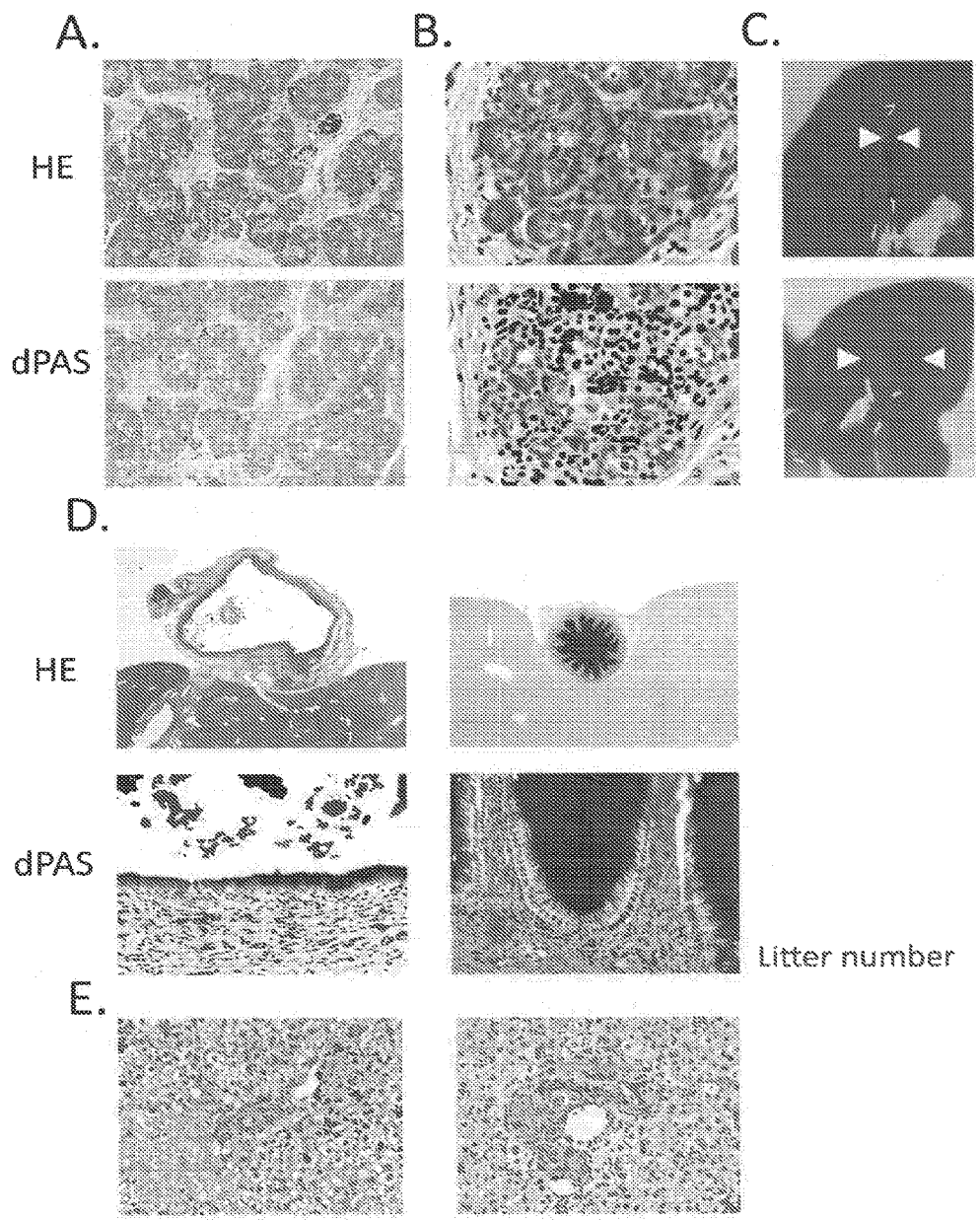
FIG. 3. (A-E) Newborn CFTR−/−; Tg-FABP-pCFTR pig pancreas. (A) Lowpower image showing loss of lobularity. (B) High-power image showing variable extent of zymogen staining (dPAS staining) in acinar cells. (C) Gross images of CFTR−/−; Tg-FABP-pCFTR gallbladders. Gallbladders ranged in size from only a few mm (left panel) to moderate sized (right panel) in cross sectional diameter. Bar=7.7 mm. (D) Microscopic images of CFTR−/−; Tg-FABP-pCFTR gallbladders. Gallbladders varied from moderate sized and patent with focal mucous change in the epithelium to severe microgallbladder that was obstructed by mucus with diffuse mucinous change in the epithelium. (E) Microscopic images of livers from CFTR−/−; Tg-FABP-pCFTR newborn pigs. There was minimal evidence (left panel) of portal change to prominent focal biliary cirrhosis-like changes (right panel).

Finally, in all of the lines studied, we observed a similar degree of pancreatic destruction (FIGS. 3A-3B), microgallbladder (FIGS. 3C-3D), and focal biliary cirrhosis (FIG. 3E) as previously reported in CFTR−/− and CFTRΔF508/ΔF508 newborn piglets (Rogers et al., Science 321:1837-1841, 2008; Stoltz et al., Sci. Transl. Med. 2:29ra31, 2010; Meyerholz et al., Am. J. Pathol. 176:1377-1389, 2010; Ostedgaard et al., Sci. Transl. Med. 3:74ra24, 2011). These findings demonstrate that the FABP-pCFTR transgene did not correct the extra-intestinal CF manifestations typically observed in the digestive system of newborn piglets and humans with CF.

CFTR is Not Present in the Airways of CFTR−/−; TgFABP-pCFTR Pigs

Figure 4:
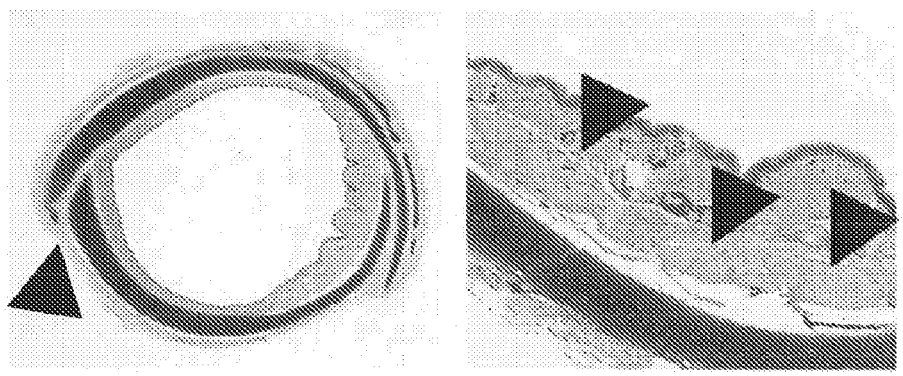
FIG. 4. Microscopic images of trachea from a CFTR−/−; Tg-FABP-pCFTR newborn pig. The tracheas were irregularly shaped, had cartilage ring defects in the anterior trachea (left panel—arrow), and areas of abnormal-appearing airway smooth muscle bundles (right panel—arrows) (Meyerholz et al., Am. J. Resp. Crit. Care Med. 182:1251-1261, 2010).

In mice, endogenous iFABP expression is localized to the intestinal tract. However, when hCFTR was expressed under control of the rat iFABP promoter in CFTR-null mice, in certain lines some extra-intestinal hCFTR expression was observed, including in the lungs (Zhou et al., Science 266:1705-1708, 1994). Therefore, we next determined if CFTR was being expressed in the airways of CFTR−/−; TgFABP-pCFTR pigs. On gross examination, CFTR−/−; TgFABP-pCFTR tracheas had narrowed airway lumens and cartilaginous ring defects as previously observed in neonatal pigs and humans with CF (Meyerholz et al., Am. J. Resp. Crit. Care. Med. 182:1251-1261, 2010) (FIG. 4). These findings were present in all lines (lines 1a-1e) studied. Using immunostaining for CFTR in newborn piglet CFTR+/+ tracheas, we found that CFTR localized to the apical membrane component of airway epithelial cells. No CFTR was detected in CFTR−/− or CFTR−/−; TgFABP-pCFTR tracheas.

Figure 5:
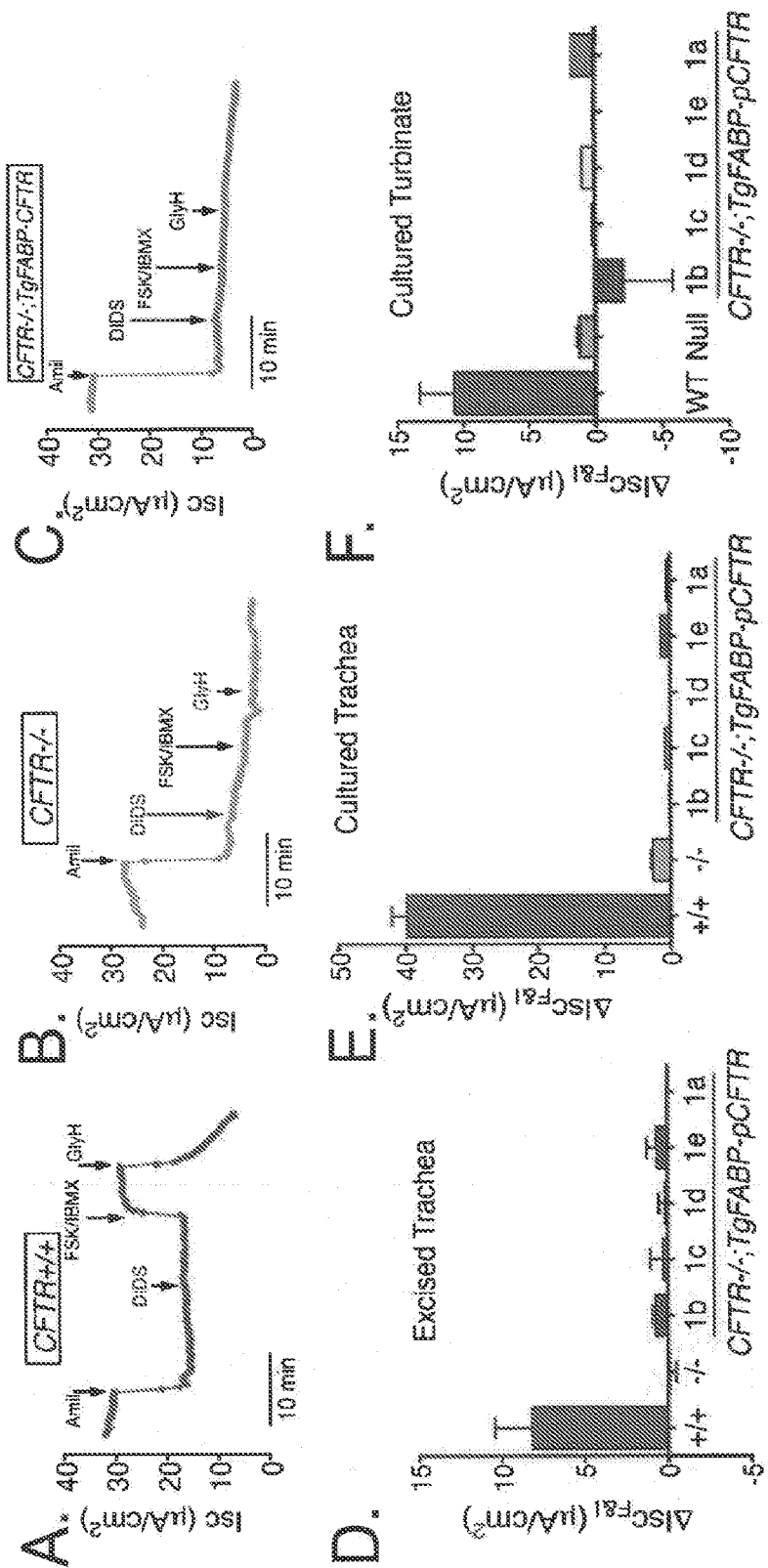
FIG. 5. (A-C) Representative Isc tracings from excised tracheas mounted in Ussing chambers for electrophysiological studies. Tracheal samples were obtained from newborn piglets. The following agents were added sequentially: apical 100 µm amiloride, apical 100 µm DIDS, apical 100 µm forskolin(FSK)/10 µm IBMX, and apical 10 µm GlyII. (D-F) Changes in Isc following addition of FSK/IBMX to (D) freshly excised tracheal segments from newborn CFTR+/+ (n=10), CFTR−/− (n=8), and CFTR−/−; TgFABP-pCFTR (n=3 for 1b, 2 for 1c, 4 for 1d, 4 for 1e, and 1 for 1a) piglets; (E) cultured tracheal epithelia from newborn CFTR+/+ (n=44), CFTR−/− (n=15), and CFTR−/−; TgFABP-pCFTR (n=1 for all cell lines except for 1d in which a sample was unavailable) piglets; and (F) cultured nasal turbinate epithelia from newborn CFTR+/+ (n=*), CFTR−/− (n=*), and CFTR−/−; TgFABP-pCFTR (n=3 for 1b, 1 for 1c, 1 for 1d, 2 for 1e, and 1 for 1a) piglets. Prior to FSK/IBMX treatment, tissues were sequentially exposed to amiloride and DIDS. Bars represent mean±SEM.

We next harvested fresh tracheal tissue from newborn piglets, mounted the excised tissue in Ussing chambers, and measured transepithelial currents to confirm the absence of CFTR-mediated CF currents in CFTR−/−; TgFABP-pCFTR tracheas. Tracheal tissues were obtained from at least one piglet from each of the transgenic lines studied. Following amiloride addition, to block epithelial Na⁺ channels, we added 4,4'-diisothiocyanostilbene-2,2'-disulfonic acid (DIDS) to block non-CFTR Cl⁻ channels, followed by forskolin and IBMX treatment to assess CFTR function. Forskolin and IBMX treatment significantly increased Isc in CFTR+/+ tracheas, but failed to increase Isc in CFTR−/− or any of the tracheas from the different CFTR−/−; TgFABP-pCFTR transgenic lines (FIGS. 5A-D). We performed similar measurements on cultured tracheal and nasal turbinate epithelium from CFTR+/+, CFTR−/−, and CFTR−/−; TgFABP-pCFTR pigs and found qualitatively very similar results to the excised tracheal studies (FIGS. 5E-F). These findings show that with this iFABP-pCFTR construct, we observe no CFTR expression in the proximal airways. These findings are important because they suggested that the CFTR−/−; TgFABP-pCFTR pigs might go on to develop lung disease similar to the CFTR−/− and CFTRΔF508/ΔF508 pigs (Stoltz et al., Sci. Transl. Med. 2:29ra31, 2010; Ostedgaard et al., Sci. Transl. Med. 3:74ra24, 2011).

CFTR−/−; TgFABP-pCFTR Pigs Develop Lung Disease Similar to Humans with CF

Of the 21 piglets treated with enemas (from 5 different transgenic lines), the bowel obstruction was relieved in 5 animals (from lines 1a and 1e) and all of these animals lived greater than 5 days (Table 2). 2 of these animals (cases #1 and #2) were euthanized at 6 days of age due to sepsis. Microbiologic cultures were positive for *Klebisella pneumoniae* in both of these animals. In subsequent surviving piglets, we treated animals with daily antibiotics for the first 7-14 days of life to minimize infectious complications.

TABLE 2

| CASE | SEX | GENOTYPE | TRANSGENIC LINE | AGE | REASON FOR EUTHANASIA |
|---|---|---|---|---|---|
| 1 | Male | CFTR−/−; TgFABP-pCFTR | 1a | 6 d | Sepsis (*Klebsiella*) |
| 2 | Male | CFTR−/−; TgFABP-pCFTR | 1a | 6 d | Sepsis (*Klebsiella*) |
| 3 | Male | CFTR−/−; TgFABP-pCFTR | 1e | 62 d | Gastric ulcer |
| 4 | Male | CFTR−/−; TgFABP-pCFTR | 1e | 332 d | Elective |
| 5 | Male | CFTR−/−; TgFABP-pCFTR | 1e | 435 d | Elective |

Figure 6:
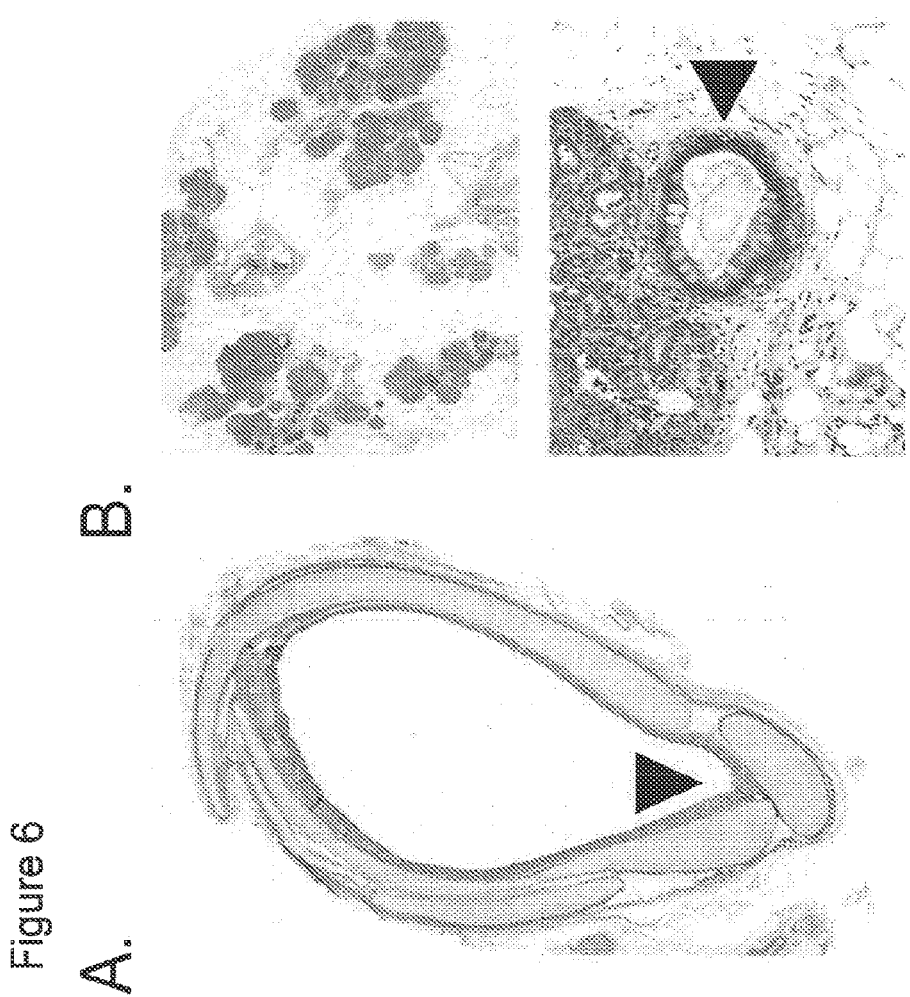
FIG. 6. Case #3 (62 d). (A) Low-power microscopic image of the trachea. The trachea is malformed in shape with anterior cartilagenous ring defects (arrow) and significant overlap of cartilage rings in the posterior trachea. (B) Microscopic images of the pancreas, top panel (2×), bottom panel (20×). Fibroadipose tissue replacement of the pancreas was prominent (top) with dilated ducts (bottom) and acini detected. (C) others had evidence of severe bridging cirrhosis (right panels). (D) Microscopic images of the liver from case #3 (62 d). At necropsy, the changes in the liver were heterogeneous. Some regions were normal-appearing (left panels) and others had evidence of severe bridging cirrhosis (right panels). Brown staining is for smooth muscle alpha-actin. (E) Microscopic images of the liver from case #3 (62 d). At necropsy the changes in the liver were heterogenous. Some regions were normal-appearing (left panels) and others had evidence of severe bridging cirrhosis (right panels). Red picrosirius staining for collagen.
Figure 6E:
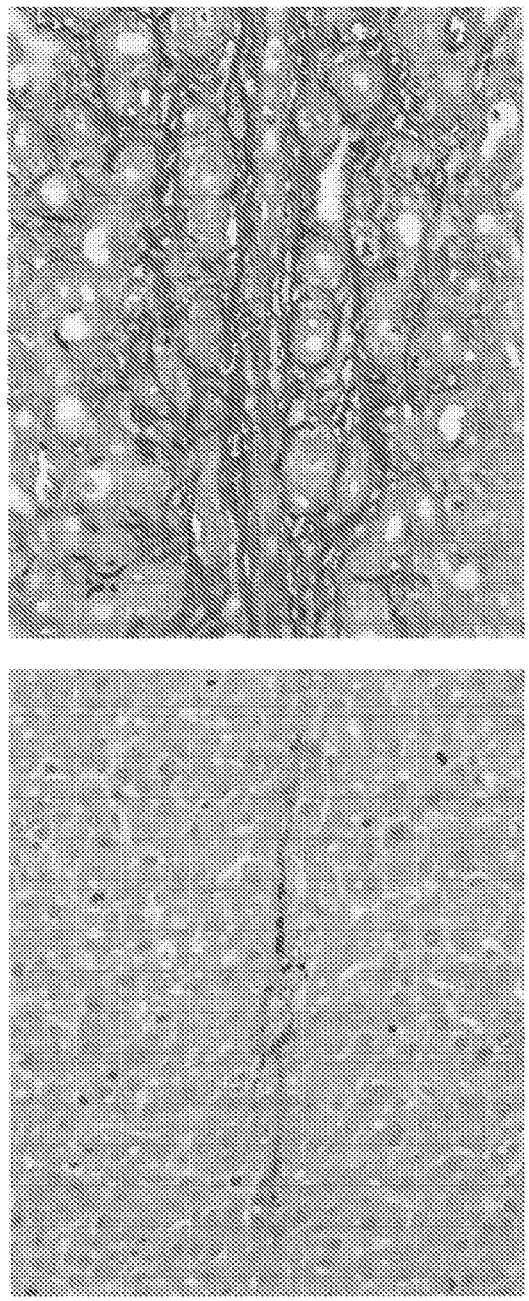

Our third surviving piglet (case #3) was euthanized at 62 days of age due to signs of respiratory disease. The trachea was irregularly shaped, similar in appearance to newborn CF pig tracheas, and defects in the cartilage rings were present (Meyerholz et al., Am. J. Resp. Crit. Care. Med. 182:1251-1261, 2010) (FIG. 6A). Necropsy showed a large gastric ulcer that had perforated into the left pleural space with evidence of a polymicrobial infection (gastrointestinal etiology) in the lung parenchyma, making interpretation of the CF-related lung disease difficult. Swine are particularly susceptible to gastric ulcers and these have been linked to respiratory disease (Trobo et al., J. Med. 25:251-254, 1994). We have previously reported a high incidence of gastric ulcers in both CFTR−/− and CFTRΔF508/ΔF508 pigs (Stoltz et al., Sci. Transl. Med. 2:29ra31, 2010; Ostedgaard et al., Sci. Transl. Med. 3:74ra24, 2011). In addition to the gastric ulcer, the liver showed changes of focal biliary cirrhosis (FIGS. 6C-E) and there was fibroadipose tissue replacement of the pancreas with prominent dilated ducts and acini (FIG. 6B).

Figure 8A:
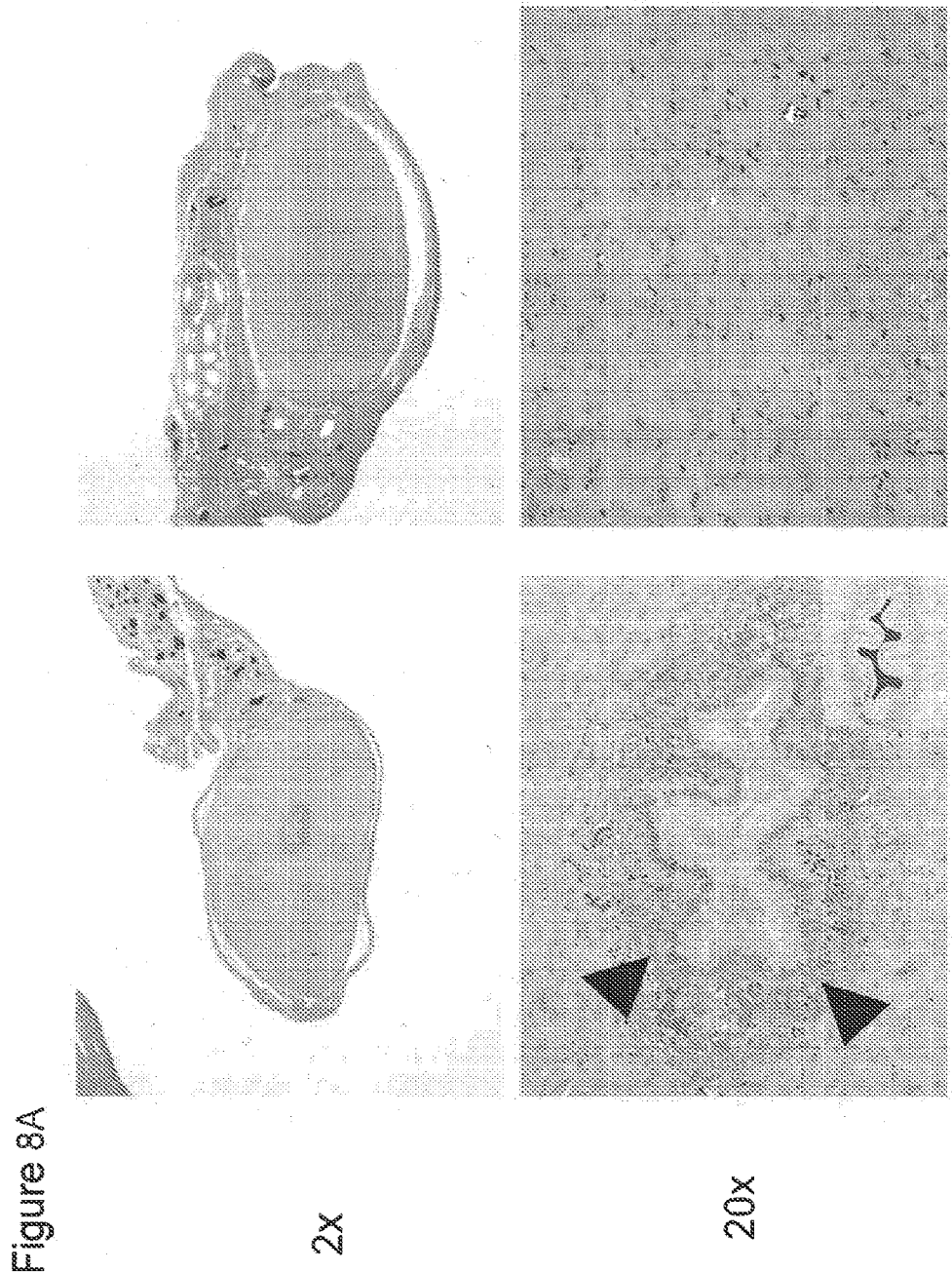
FIG. 8. (A) Microscopic images of the vas deferens from case #5 (435 d). The vas deferens epithelium (arrow, left lower panel), when detected, was often collapsed with eosinophilic material in the lumen that was dPAS positive (inset) or more often completely absent (right panels). (B) Microscopic images of the vas deferens from case #5 (435 d) with different stains (20×).
Figure 8B:
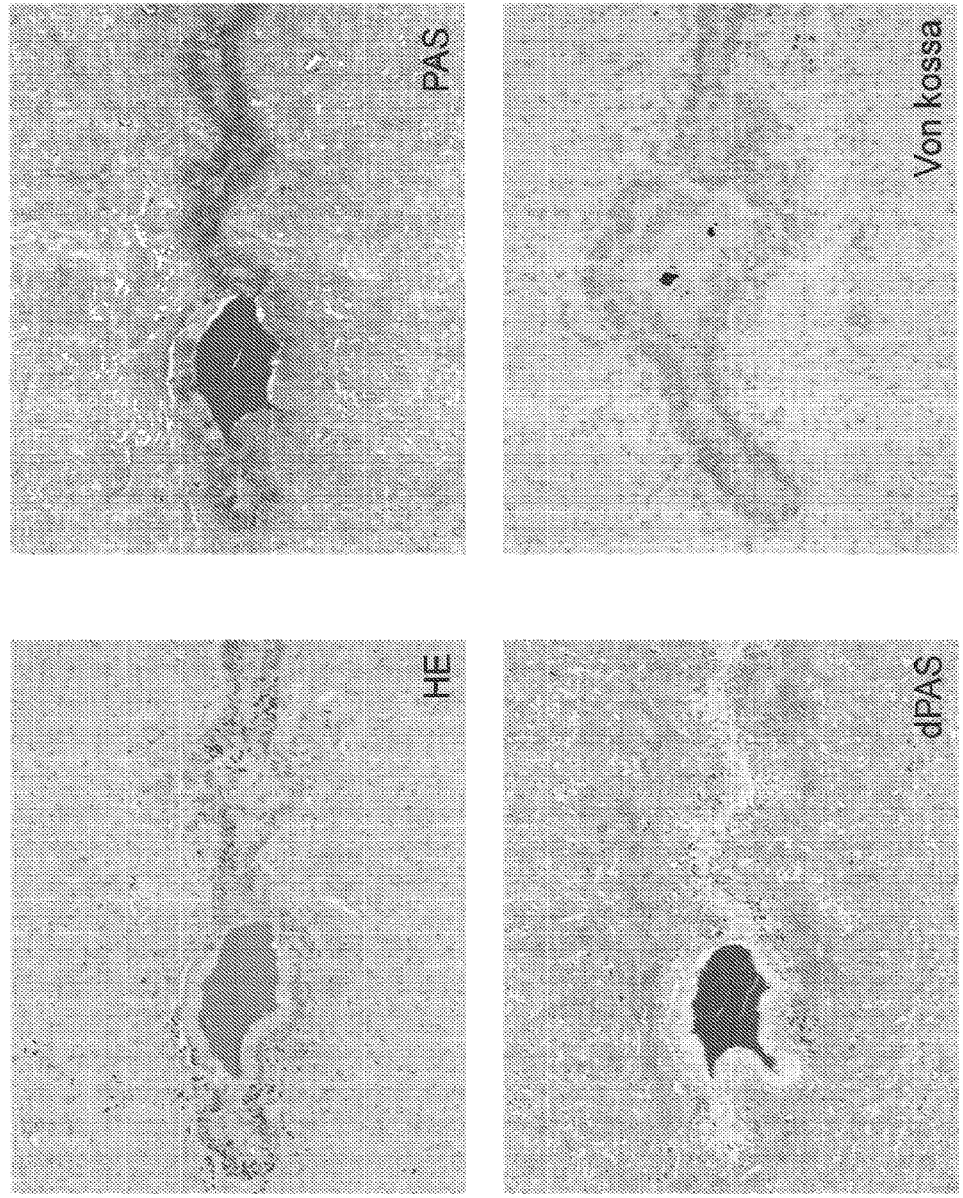

The two remaining CFTR−/−; TgFABP-pCFTR pigs were electively euthanized at 332 (case #4) and 435 (case #5) days. Both animals had evidence of progressive loss of pancreatic exocrine tissue and replacement by adipose tissue, similar to older CFTR−/− and CFTRΔF508/ΔF508 pigs (Stoltz et al., Sci. Transl. Med. 2:29ra31, 2010; Ostedgaard et al., Sci. Transl. Med. 3:74ra24, 2011) (FIGS. 7A-D). The gallbladders were small in size from case #4 and #5. The lumen of case #5's gallbladder was filled with mucopurulent and necrotic cellular debris (FIGS. 7E-G) and the lumen of case #4 was also filled with mucus and inflammatory cells were present. We also observed variable changes along the length of the vas deferens in both case #4 and #5. In some areas of the vas deferens, the lumen was collapsed and filled with eosinophilic material that was PAS-positive, but more commonly the lumen was completely absent (FIGS. 8A and 8B).

Figure 9:
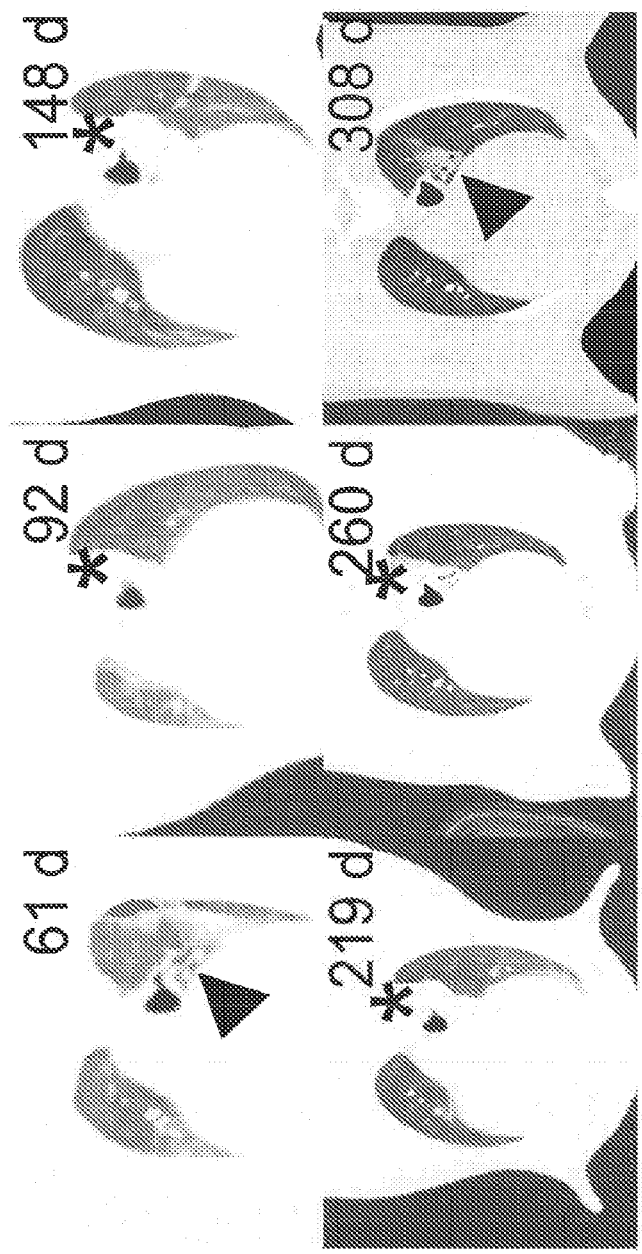
FIG. 9. (A) Serial chest X-ray computed tomography images from a CFTR−/−; TgFABP-pCFTR pig (case #5). Airway wall thickening (arrows) was present. At 92 d, obstruction of the tracheal bronchus was observed with collapse of the associated lung segment (asterisks). This persisted until 260 d and was resolving by 308 d. Airway wall thickening and parenchymal changes persisted. (B and C) Total number and different bacterial species recovered in serial tracheal lobe BAL samples from two CFTR-I-; TgFABP-pCFTR pigs Case #4 (B and C) and Case #5 (D and E). Data are color-coded to indicate individual species of bacteria. (F and G) Bronchoalveolar lavage (BAL) neutrophil and 11-8 levels in a CFTR−/−; TgFABP-pCFTR pig (case #5). BAL was performed at indicated time points and (F) percent neutrophils and (G) 11-8 were determined on recovered liquid from the tracheal lobe.
Figure 9:
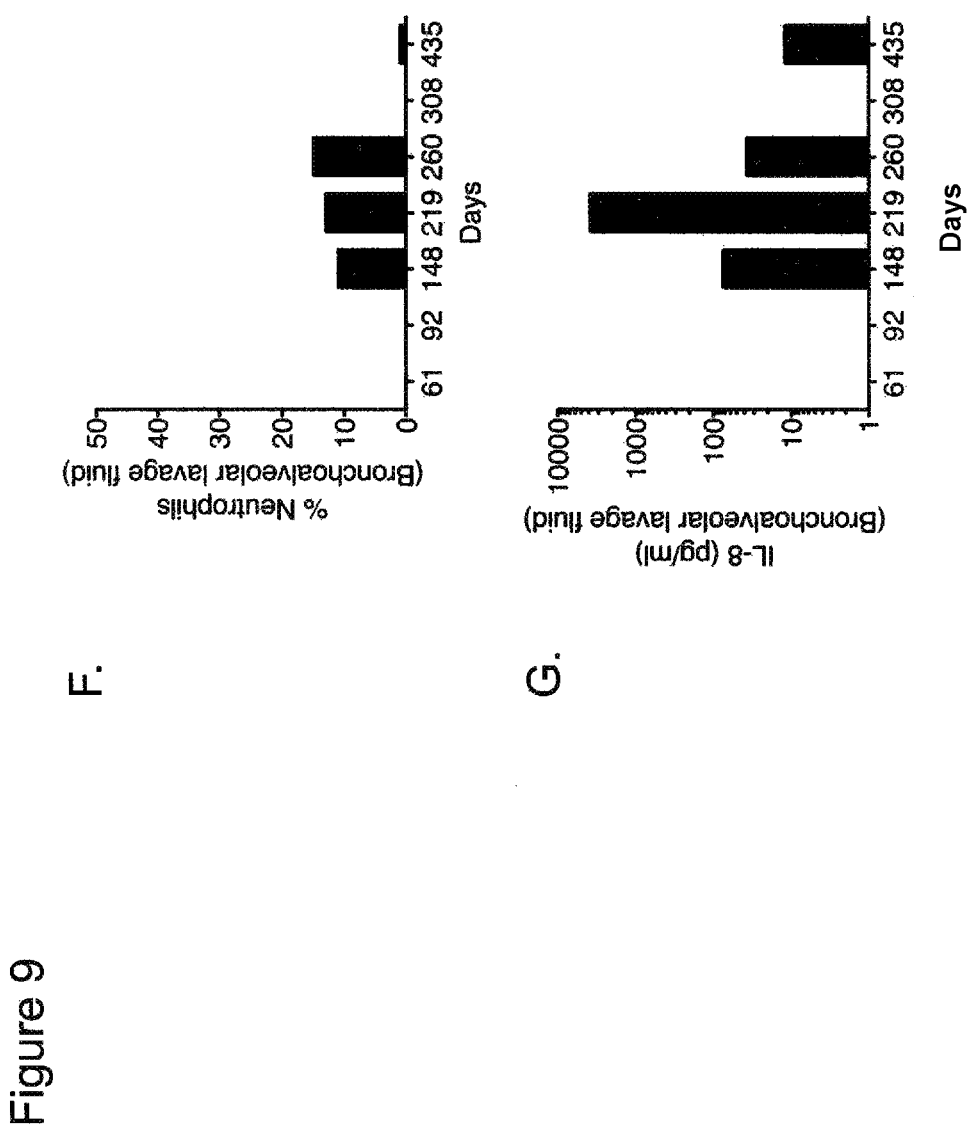

Both pigs had variable evidence of lung disease at necropsy and on serial chest CTs. Lung disease tended to be most evident in the tracheal lobe and FIG. 9A shows serial chest CT images of the tracheal lobe region from case #5 at 61, 92, 148, 219, 260, and 308 days of age. There was evidence of progressive involvement of the tracheal lobe with airway wall thickening, patchy infiltrates, and progressive collapse of a subsegment of the tracheal lobe. Over time some of these changes were variably present, while others (airway wall thickening) seemed to remain.

Serial bronchoscopy with bronchoalveolar (BAL) lavage was performed on these two animals to look for evidence of airway infection and inflammation. Culture of BAL liquid showed variable numbers of bacteria in samples from these two animals over time. In all but two of the BAL liquid samples (both from case #5), at least $10^2$ cfu/ml of total bacteria was cultured (FIGS. 9B and 9D). A number of different bacterial species were cultured from the BAL liquid (FIGS. 9C and 9E). Of note, *Pseudomonas aeruginosa* was cultured from the BAL liquid of one pig (case #5) at three different time points (FIG. 9E) with the greatest amount being present on the first BAL. *P. aeruginosa* is a common bacterial pathogen isolated from the lungs of humans with CF and this is the first time that we have isolated *P. aeruginosa* from lungs of a CF pig (CFTR−/− or CFTRΔF508/ΔF508). Interestingly, the absolute number of *P. aeruginosa* cultured from the BAL liquid changed over time and following the first isolation of *P. aeruginosa* from BAL liquid samples, not all subsequent samples were positive for *P. aeruginosa*; despite lack of antibiotic use for eradication of the pathogen. *Streptococcus suis*, a common respiratory pathogen in swine, was also isolated in large numbers from case #5 on day 219 (FIG. 9E).

In one of the two older animals (case #5), we found that the percentage of neutrophils recovered from the BAL liquid increased on days 148, 219, and 260 (FIG. 9F). Interestingly, these levels correlated with worsening radiographic abnormalities on the chest CT, increasing BAL liquid bacterial counts, and elevated IL-8 levels (FIGS. 9A, 9D, and 9G).

Materials and Methods

CFTR−/−; TgFABP-pCFTR Vector Construction

For generation of CFTR−/−; TgFABP-pCFTR pigs, we transfected fetal fibroblasts with a transgenic construct containing the rat iFABP promoter (a gift from Jeffrey Gordon, Washington University, St. Louis, Mo.) and porcine CFTR. Using the pCI vector (Promega), we first substituted the CMV promoter with the nucleotide sequence −1178 to +28 of the rat iFABP promoter. The porcine CFTR sequence was amplified from pcDNA3.1-Kozak-pCFTR plasmid using NheI and XhoI and inserted into the redesigned pCI-iFABP vector with the same enzymes. Plasmid pcDNA3.1(+)Hygro (Invitrogen) was digested with NruI and EcoRV to remove the CMV promoter (pcDNA3.1(+)HygroΔCMV). The iFABP-CFTR fragment was amplified from pCI-iFABP-pCFTR with PfuUltra Polymerase (Stratagene) and ligated with pcDNA3.1(+)HygroΔCMV. Restriction and sequence analysis was performed on the redesigned plasmid prior to use for transfection of fetal fibroblasts (FIG. 1E).

Fetal Fibroblasts

We previously reported generation of CFTR−/− pigs (Rogers et al., Science 321:1837-1841, 2008). Fetal fibroblasts were isolated from day 35 CFTR−/− fetuses as previously described. Cells were grown in F10 media (Invitrogen), containing 20% FCS and penicillin/streptomycin.

Transfection, Selection, and Southern Blot Screening of Clones

Fetal CFTR−/− fibroblasts were electroporated with 15 µg of linearized DNA from the iFABP-pCFTR transgenic construct and then cultured. After 48 hours, the media was changed and supplemented with 100 µg/ml hygromycin (Invitrogen) for 14 days to select for antibiotic-resistant clones. Southern blot screening was performed on hygromycin-resistant cells as previously described (Rogers et al., J. Clin. Invest. 118:1571-1577, 2008). Briefly, amplified whole genomic DNA was prepared from each clone and 20 µg was digested with Ban II overnight. Genomic digests were electrophoresed on a 0.8% agarose gel and transferred to a positively charged nylon membrane (Roche) by using an alkaline transfer procedure. Blots were prehybridized for 30 min at 65° C. in Rapid-hyb buffer (Amersham). The blot was then hybridized in Rapid-hyb buffer with a $^{32}$P-labeled probe specific for the entire exon 13 of porcine CFTR (65° C., overnight). Two bands were anticipated on the blots: one at 2198 bp for endogenous CFTR and the other at 3542 bp for the transgenic CFTR.

Production of Transgenic Animals

Cryopreserved clones were thawed and resuspended in micromanipulation media. Oocyte maturation, somatic cell nuclear transfer, surrogate preparation, and embryo transfer were all performed as previously described (Rogers et al., J. Clin. Invest. 118:1571-1577, 2008). The University of Iowa and University of Missouri Animal Care and Use Committees approved all animal studies.

Care of Pigs

A cesarean section was performed to recover the piglets on days 116-118. After delivery the piglets were provided medical care and fed colostrum containing polyethylene glycol 3350. Shortly after birth, most piglets underwent a gastrograffin enema. This was repeated every 8-12 hours until all meconium was evacuated or the enemas failed to induce a response. Piglets were initially raised on milk replacer until mature enough to be placed on standard pig diets. In some litters, piglets received daily antibiotics for the first 7-14 days of life (ceftiofur, 5 mg/kg, IM). All animals received: a) oral pancreatic enzyme replacement therapy (PancreVed, Vedco) with meals (4000 IU lipase/120 mL milk replacer or ~10,000 IU lipase/kg/day divided between meals). b) oral fat-soluble vitamins (PancreVed, Vedco). c) oral proton pump inhibitor (1 mg/kg) (omeprazole, Sandoz) once a day. d) oral polyethylene glycol 3350 (Paddock Laboratories, MinncapPharmaceuticals) with each meal titrated to maintain soft stools.

Bronchoalveolar Lavage Liquid Collection and Analysis

For bronchoalveolar lavage (BAL) in the older pigs, animals were anesthetized with ketamine (15-20 mg/kg, IM), xylazine (1-1.5 mg/kg, IM), and intravenous propofol. A flexible fiberoptic bronchoscope (Pentax FB-10X; Montvale, N.J.) was inserted orally and passed through the vocal cords. The suction channel was not used until the tip of the bronchoscope was past the vocal cords. The bronchoscope tip was gently inserted and wedged into the tracheal bronchus airway. Three aliquots (10 ml each) of sterile saline were instilled into the airway and lavage liquid was recovered with intermittent suction. The BAL liquid was pooled and immediately placed on ice, transported to the laboratory for processing (cell counts and microbiology studies) and stored at −80° C. for subsequent analysis.

The total number of recovered cells in BAL liquid was quantified with a hemacytometer and morphologic differentiation of cells was performed on cytospin preparations that were stained with Diff-Quick Stain kit (Baxter). Microbiologic studies were performed on collected BAL liquid, and IL-8 levels were determined on recovered supernatant after centrifugation (1600×g for 10 min) using a standard sandwich ELISA (R&D Systems).

CT Scanning

All chest X-ray computed tomographic (CT) imaging was performed on sedated, spontaneously breathing animals using a 64-slice high-resolution CT (HRCT) scanner (SOMATOM 64, Siemens, Malvern, Pa.).

Production of Primary Cultures of Differentiated Airway Epithelia

Epithelial cells were isolated from tracheas and nasal turbinates by enzymatic digestion, seeded onto permeable filter supports, and grown at the air-liquid interface as previously described. Differentiated epithelia were used at least 14 days after seeding.

Histopathological Analysis

At necropsy, pigs were examined for gross lesions and the findings were documented. Tissues were fixed in 10% neutral buffered formalin for 48-96 hr. Tissues were then routinely processed, embedded, sectioned (4 µm), and stained with hematoxylin and eosin (HE) for general examination.

Microbiologic Studies

Standard microbiologic techniques were utilized to identify and quantify bacteria present in bronchoalveolar lavage liquid samples. Samples were serially diluted and plated onto blood agar (tryptic soy agar with sheep blood; Remel), Colombia colistin-nalidixic acid agar (Remel), Chocolate agar (Remel), Mannitol Salt Agar (Remel), MacConkey agar (Remel), and *Burkholderia cepacia* selective agar (Remel). Organisms were identified with standard microbiological procedures. Some identifications were confirmed by API 20E or API 20NE (bioMérieux), Vitek (bioMérieux) or 16S rRNA gene sequencing (University of Iowa Clinical Microbiology Laboratory and Iowa State University Diagnostic Laboratory).

Quantitative RT-PCR

Quantitative RT-PCR used TaqMan chemistry and an ABI 7500 Fast Real-time PCR System to measure porcine CFTR mRNA. Briefly, tissue was collected in RNAlater (Ambion) and total RNA was isolated as above. First-strand cDNA was synthesized with random hexamers (SuperScript III, Invitrogen). Sequence-specific primers and probes for porcine CFTR and b-actin were from ABI. For measuring CFTR mRNA, primer/probe sets annealing to exon 10 of CFTR (Ss03389420_m1, pCFTR) and b-actin (Ss03376160_u1, ACTB) were used in separate reactions. Amounts of CFTR mRNA were normalized to β-actin. This normalized value for each tissue expressed relative to normalized CFTR$^{++}$ duodenum to calculate the % of mRNA relative to wild-type duodenum (100%).

Immunoprecipitation and Phosphorylation

Protein assays were performed using the BCA assay (Thermo-Fisher). Indicated amounts of intestinal tissue or cells from 1-2 trachea were homogenized in the Tris-mannitol buffer on ice with 20 strokes of the loose-fitting and 15 strokes of the tight-fitting pestle of a Potter-Elvejehm homogenizer. Membrane pellets were isolated by centrifugation at 200,000×g at 4° C. for 30 min. The pellets were solubilized in a commercial detergent mix, Membrane Solution 2 (Profoldin, Ca). Soluble proteins were separated from insoluble pellets by centrifuging at 200,000×g for 20 min. CFTR was immunoprecipitated from the supernatant of soluble proteins with anti-CFTR antibodies M3A7 and MM13-14 (Upstate Biotechnology) and in vitro phosphorylated with $^{32}$P-ATP and the catalytic subunit of PKA (Promega). Washed precipitates were electrophoresed on 6% SDS-PAGE. Gels were stained, destained, dried and exposed to phosphoscreens before imaging on a Fuji FLA7000 imager (General Electric).

Immunocytochemistry

Intestinal and tracheal tissues were excised from newborn piglets, immediately placed in ice-cold 30% sucrose, and quick-frozen in OCT with liquid $N_2$. Tissue segments were kept at −80° C. Tissues were cryosectioned into 7 μm sections, fixed in 100% MeOH at −20° C. for 10 min, permeabilized in 0.2% TX-100 (Thermo-Fisher) in PBS, and blocked in Super-Block (Thermo-Fisher) with 5% normal goat serum (Jackson ImmunoResearch). Tissue sections were incubated for 2 hrs at 37° C. in anti-CFTR antibodies MM13-4, M3A7 (Chemicon), and polyclonal antibody to the tight junction protein ZO-1 (Zymed) (all at 1:100 dilution), followed by secondary antibodies (goat-anti-mouse Alexa-Fluor488 and goat anti-rabbit Alexa-Fluor568; Molecular Probes/Invitrogen) (1:1000 dilution). Sections were mounted with Vectashield (Hard-set) containing DAPI (Vector Labs) to visualize nuclei. Images were acquired with identical parameters on an Olympus Fluoview FV1000 confocal microscope with a UPLSAPO 60× oil lens. Images were scanned sequentially at 2 msec/pixel.

Electrophysiological Measurements of Freshly Excised and Cultured Epithelia

Epithelial tissues were excised from the nasal turbinate and trachea immediately after animals were euthanized. Tissues and cultured epithelia were studied in modified Ussing chambers. Epithelia were bathed on both surfaces with solution containing (mM): 135 NaCl, 2.4 $K_2HPO_4$, 0.6 $KH_2PO_4$, 1.2 $CaCl_2$, 1.2 $MgCl_2$, 10 dextrose, 5 HEPES, pH 7.4, at 37° C. and gassed with compressed air. Transepithelial voltage (Vt) was maintained at 0 mV to measure short-circuit current (Isc). Transepithelial electrical conductance (Gt) was measured by intermittently clamping Vt to +5 and/or −5 mV.

A standard protocol was the following. 1) Measurements under basal conditions. 2) 100 mM apical amiloride to inhibit ENaC $Na^+$ channels. 3) 100 mM apical DIDS (4,4-diisothiocyano stilbene-2,2-disulfonic acid) to inhibit most anion channels other than CFTR. 4) 10 mM forskolin and 100 mM IBMX (3-isobutyl-2-methylxanthine) to increase cellular levels of cAMP leading to phosphorylation and activation of CFTR. 5) 100 mM apical GlyH-101 to inhibit CFTR. 6) 100 μM bumetanide to inhibit basolateral Na—K-2Cl transporter in cultured epithelia.

Other Embodiments

All publications, patents, and other citations noted in this specification are incorporated herein by reference as if each individual publication, patent, or other citation were specifically and individually indicated to be incorporated by reference. Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Use in the claims and elsewhere herein of singular forms, such as "a" and "the," does not exclude indication of the corresponding plural form, unless the context indicates to the contrary. Thus, for example, if a claim indicates the presence of "a" mutation in "a" gene, it can be interpreted as covering one or more mutations, in one or more genes, unless otherwise indicated. Further, the term "or" as used herein is intended to be interpreted as both optional (i.e., one or the other and not both of multiple options) and inclusive (i.e., and/or).

Other embodiments are within the following claims.

The invention claimed is:

1. A method of determining whether a candidate therapeutic approach can be used in the treatment of cystic fibrosis in a human patient, the method comprising:
   (i) carrying out the candidate therapeutic approach on a transgenic pig wherein:
      (a) the pig comprises a genome in which both of the pig CFTR alleles have been knocked out, or both of the pig CFTR alleles have been replaced with a mutant porcine or a mutant human CFTR gene comprising a deletion of F508;
      (b) the genome of the pig comprises a wild-type CFTR transgene under the control of an intestinal cell-specific promoter resulting in wild-type CFTR expression in intestinal cells of the pig;
      (c) the pig exhibits reduced meconium ileus relative to a pig lacking expression of the CFTR transgene in intestinal cells, and
      (d) the pig exhibits one or more symptoms of cystic fibrosis, and
   (ii) detecting an improvement in at least one of the one or more symptoms of cystic fibrosis in the pig, wherein said improvement indicates that the candidate therapeutic approach could be effective in the treatment of cystic fibrosis in a human patient.

2. The method of claim 1, wherein the candidate therapeutic approach comprises administration of a candidate therapeutic agent.

3. The method of claim 1, wherein the symptom of cystic fibrosis is detected in the lung, pancreas, liver, or kidney of the pig.

4. The method of claim 1, wherein the intestinal cell-specific promoter is an intestinal fatty acid binding protein (iFABP) promoter.

5. The method of claim 1, wherein both of the pig CFTR alleles of the genome of the pig have been knocked out.

6. The method of claim 1, wherein both of the pig CFTR alleles of the genome of the pig have been replaced with a mutant porcine or a mutant human CFTR gene comprising a deletion of F508.

7. The method of claim 6, wherein the mutant CFTR gene comprising a deletion of F508 is a human CFTR gene.

8. The method of claim 6, wherein the mutant CFTR gene comprising a deletion of F508 is a porcine CFTR gene.

9. The method of claim 1, wherein the pig has one or more cystic fibrosis phenotypes selected from the group consisting of (a) an electrophysiological phenotype similar to that of human cystic fibrosis, (b) pancreatic insufficiency or abnormalities, (c) hepatic abnormalities, (d) gall bladder and/or bile duct abnormalities, (e) tracheal abnormalities, (f) cystic fibrosis lung disease, (g) sweat gland abnormalities, and (h) kidney abnormalities.

10. The method of claim 1, wherein the pig exhibits one or more characteristics of cystic fibrosis in the lungs.

\* \* \* \* \*